(12) United States Patent
Maritan

(10) Patent No.: US 9,533,099 B2
(45) Date of Patent: Jan. 3, 2017

(54) AUTOMATIC INJECTION DEVICE

(71) Applicant: Becton Dickinson France, Le Pont de Claix (FR)

(72) Inventor: Lionel Maritan, Pierre-Chatel (FR)

(73) Assignee: Becton Dickinson France, Le Pont de Claix (FR)

(*) Notice: Subject to any disclaimer, the term of this patent is extended or adjusted under 35 U.S.C. 154(b) by 0 days.

(21) Appl. No.: 14/426,336

(22) PCT Filed: Aug. 28, 2013

(86) PCT No.: PCT/IB2013/002395
§ 371 (c)(1),
(2) Date: Mar. 5, 2015

(87) PCT Pub. No.: WO2014/037805
PCT Pub. Date: Mar. 13, 2014

(65) Prior Publication Data
US 2015/0250949 A1    Sep. 10, 2015

(30) Foreign Application Priority Data

Sep. 5, 2012  (EP) .................................. 12306061

(51) Int. Cl.
*A61M 5/00*  (2006.01)
*A61M 5/20*  (2006.01)
(Continued)

(52) U.S. Cl.
CPC .......... *A61M 5/2033* (2013.01); *A61M 5/3204* (2013.01); *A61M 5/326* (2013.01); *A61M 5/5086* (2013.01); *A61M 2005/206* (2013.01); *A61M 2005/208* (2013.01); *A61M 2005/3104* (2013.01); *A61M 2005/3142* (2013.01); *A61M 2005/3143* (2013.01); *A61M 2205/581* (2013.01); *A61M 2205/582* (2013.01); *A61M 2205/583* (2013.01)

(58) Field of Classification Search
CPC ............... A61M 2005/206; A61M 2005/3142; A61M 5/3204; A61M 2005/2073
USPC ......................................... 604/187
See application file for complete search history.

(56) References Cited

U.S. PATENT DOCUMENTS

2010/0312195 A1   12/2010  Johansen et al.
2011/0028910 A1    2/2011  Weber

FOREIGN PATENT DOCUMENTS

WO    2008148518 A1   12/2008
WO    2009062508 A1    5/2009

*Primary Examiner* — Kevin C Sirmons
*Assistant Examiner* — Deanna K Hall
(74) *Attorney, Agent, or Firm* — The Webb Law Firm

(57) ABSTRACT

The present invention relates to an automatic injection device (1) comprising: a container having a longitudinal axis A and movable between a first position and a second position, in which the needle is inserted, biasing means, for moving the container to its second position, retaining means (70, 73, 74) for maintaining said biasing means in a first stressed state, triggering means (90) for releasing said retaining means, said retaining means comprising a lever member having a pivoting part and a radial projection extending therefrom, said radial projection being in a first angular position when said retaining means is in its passive condition, said radial projection being in a second angular position, different from said first angular position, when said retaining means is in its active condition, the axis of said pivoting part being included in a transversal plane of said longitudinal axis A.

19 Claims, 15 Drawing Sheets

Figure 1E:
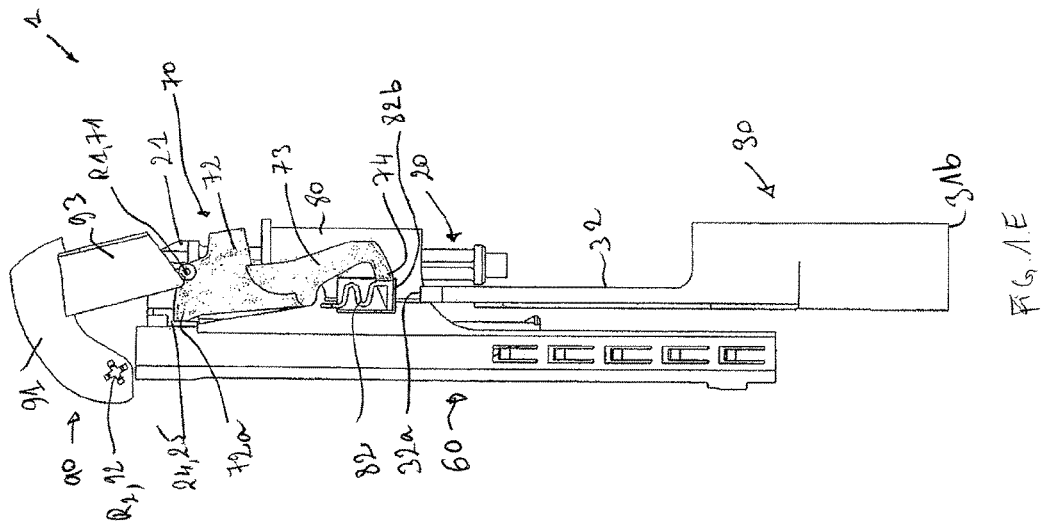

(51) Int. Cl.
   *A61M 5/32*   (2006.01)
   *A61M 5/50*   (2006.01)
   *A61M 5/31*   (2006.01)

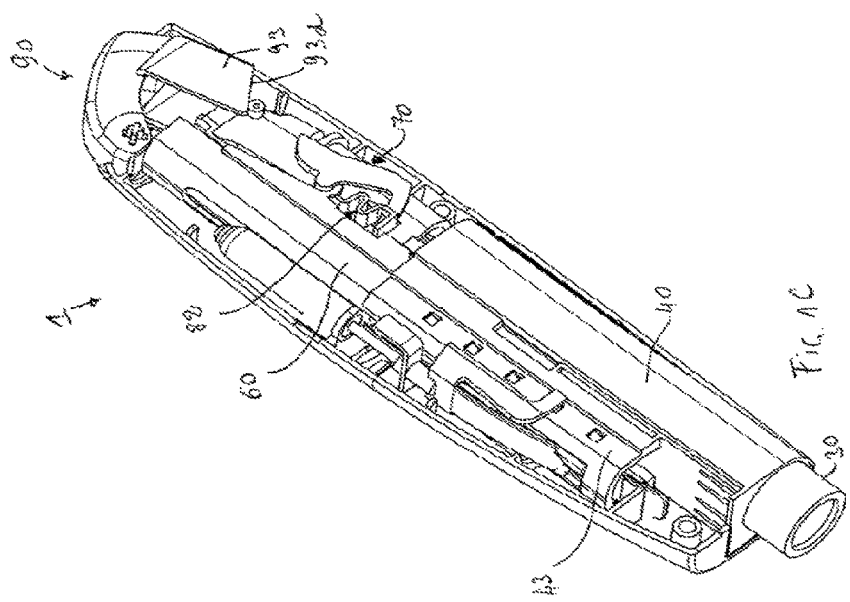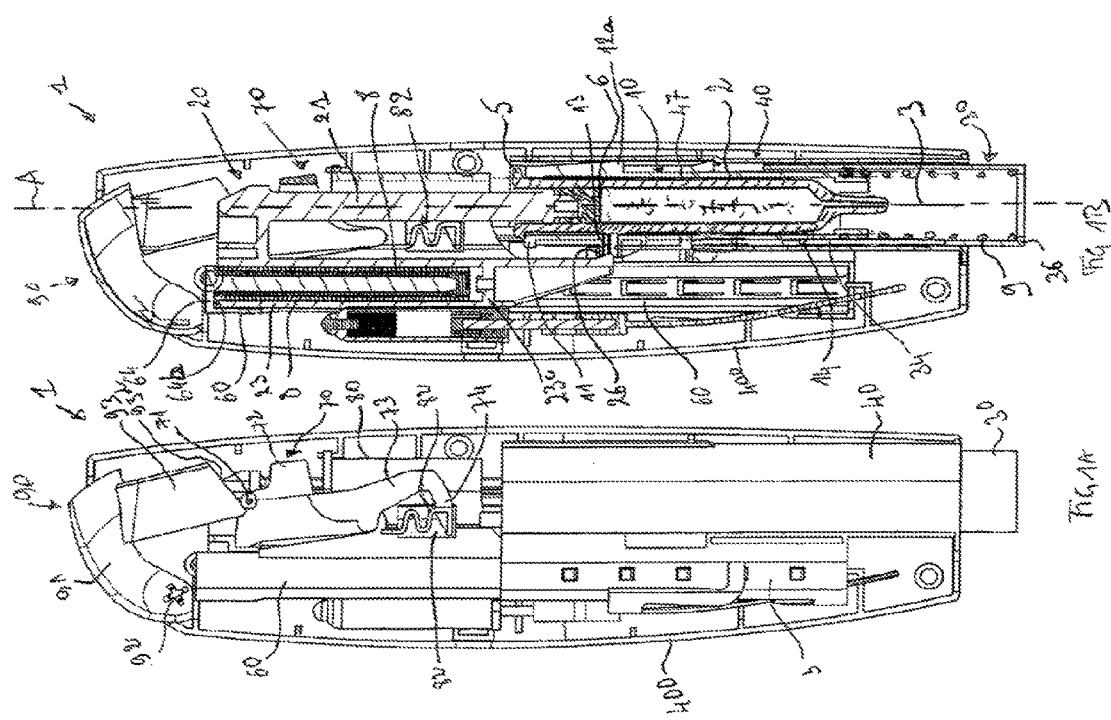

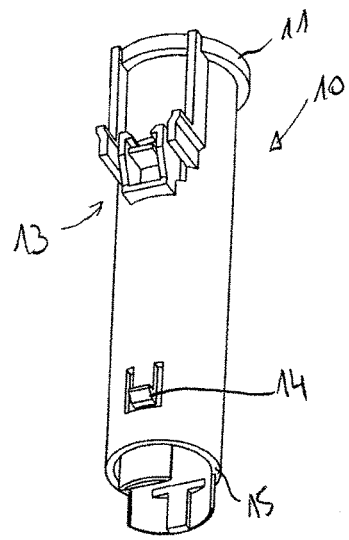
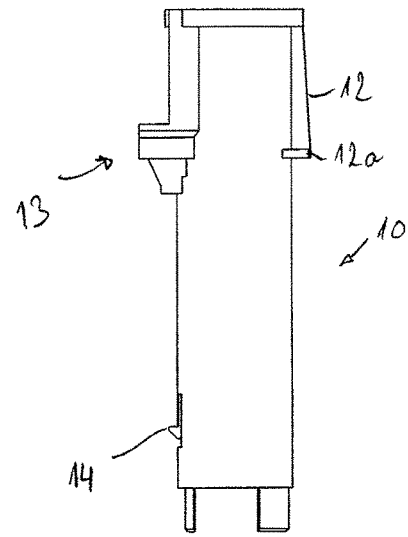
FIG. 2A
FIG. 2B
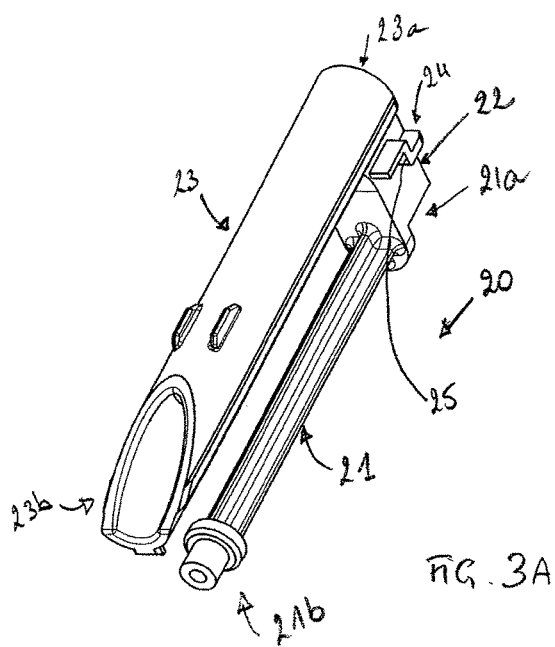
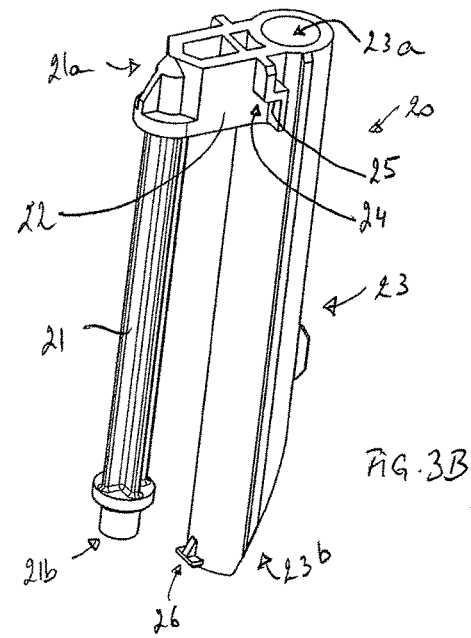
FIG. 3A
FIG. 3B

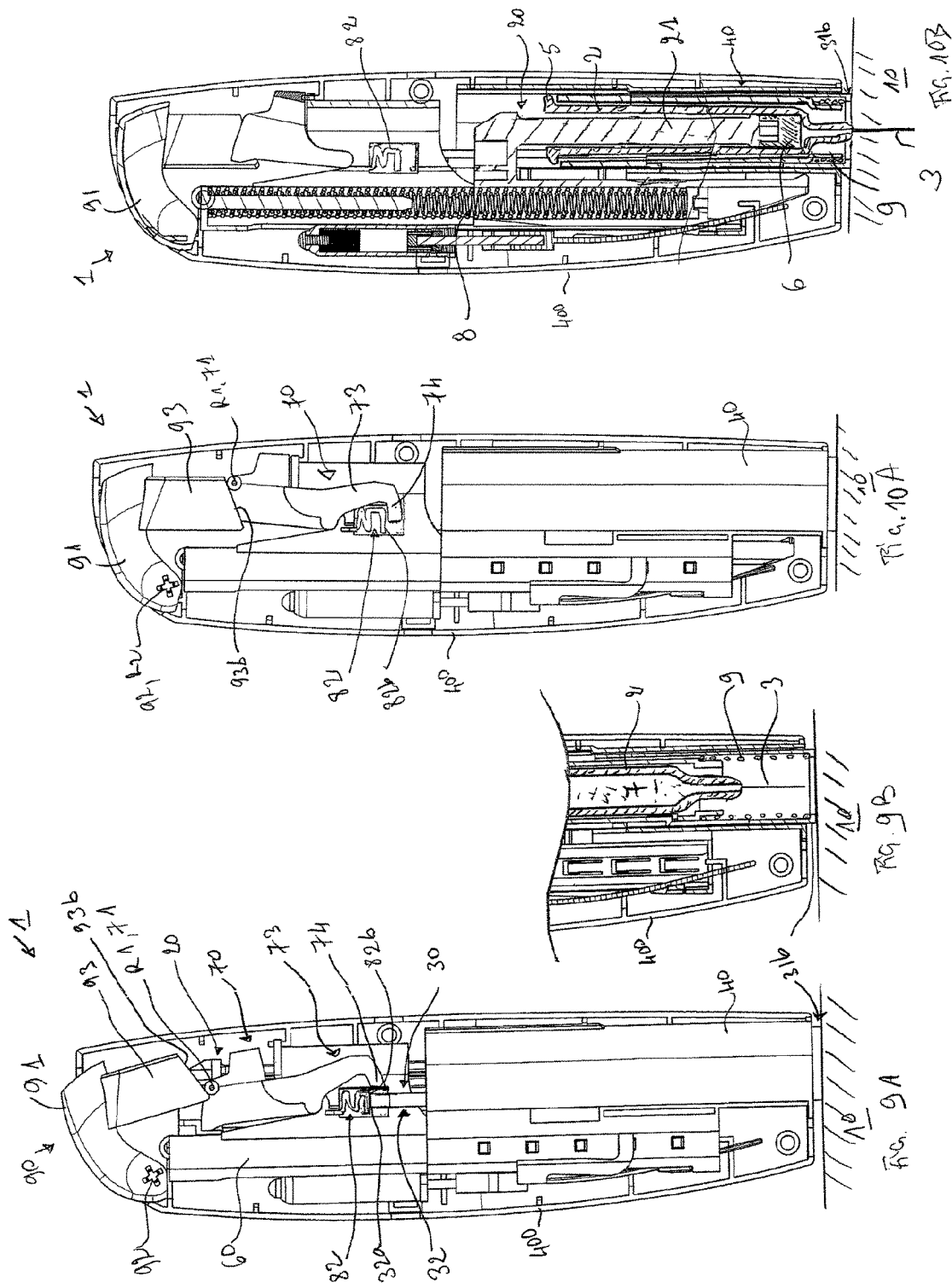

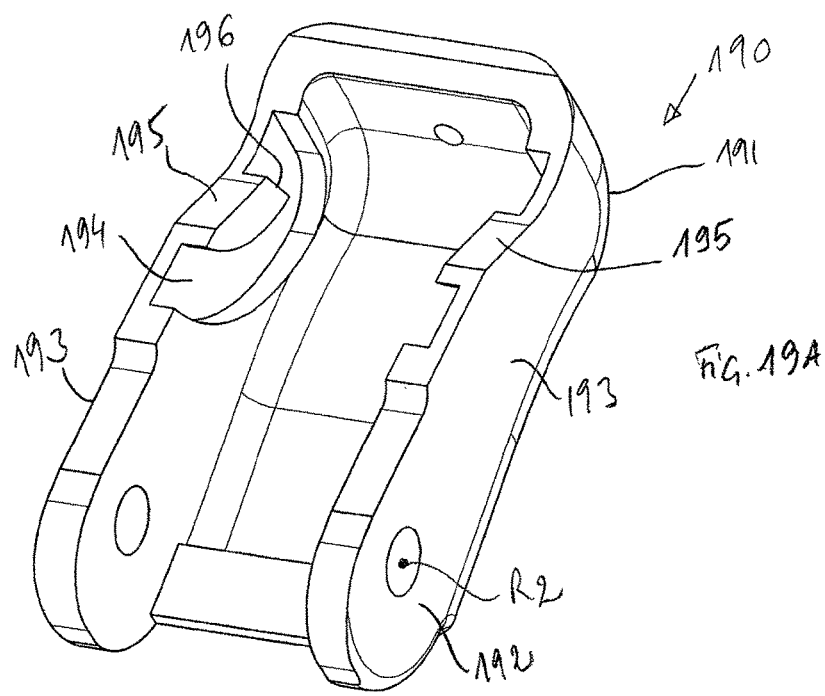
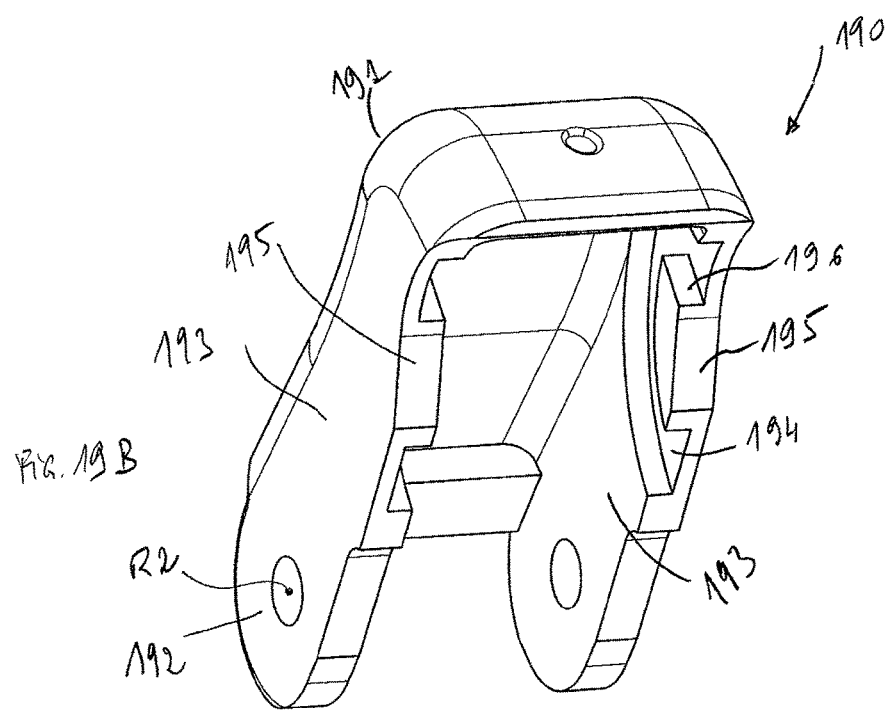

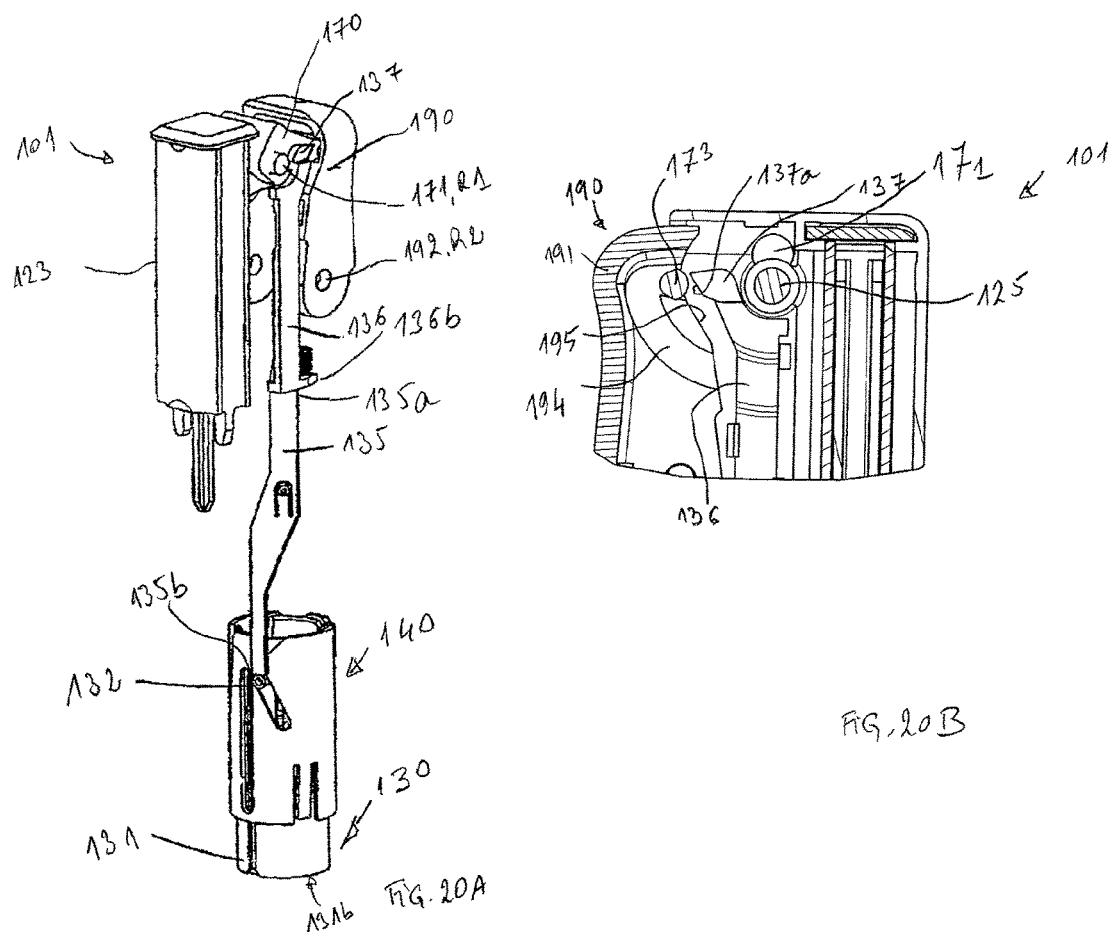
FIG. 20A
FIG. 20B
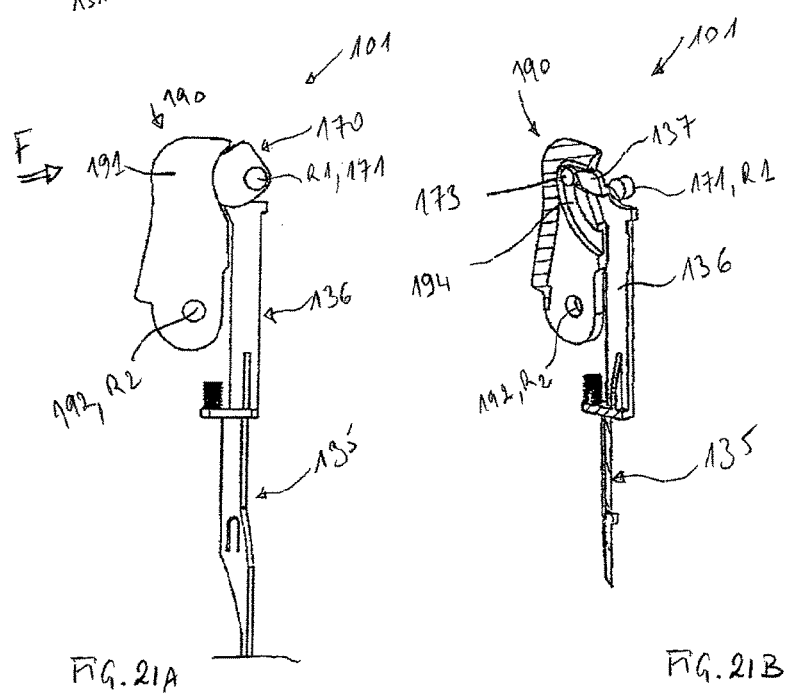
FIG. 21A
FIG. 21B

AUTOMATIC INJECTION DEVICE

CROSS-REFERENCE TO RELATED APPLICATIONS

This application is the U.S. national phase of International Application No. PCT/IB2013/002395 filed Aug. 28, 2013, and claims priority to European Patent Application No. 12306061.8 filed Sep. 5, 2012, the disclosures of which are hereby incorporated in their entirety by reference.

The present invention relates to a device for injection of a product, for which the insertion step of the needle is automated and may be completed with minimal effort from the user.

In this application, the distal end of an element or of a device means the end furthest away from the hand of the user and the proximal end means the end closest to the hand of the user, when the element or device is in the use-position. Similarly, in this application, the terms "in the distal direction" and "distally" mean in the direction of the injection, and the terms "in the proximal direction" and "proximally" mean in the direction opposite to the direction of injection.

Devices for automatic injection of a product, also called autoinjectors, are widely used in medical fields where the treatment of a pathology requires daily injections, such as the treatment of some diabetes, and where patients often proceed to these injections on their own. As patients are not professional healthcare workers, the whole process is as much as possible automated so that the patient needs not make decisions during the injection. Autoinjectors usually comprise on one hand a container having a needle and filled with the product to be injected, such as a prefilled syringe for example or a cartridge, and on the other hand a motor part, in other words a part comprising the various systems which will trigger the insertion of the needle, realise the injection and potentially activate a protection system at the end of injection.

Most of the already existing autoinjectors comprise at least a system for automatically inserting the needle into the patient's skin, and triggering means for initiating such an insertion of the needle, the triggering means being intended to be activated by the patient when he is ready. Nevertheless, most of the automatic insertion systems of the autoinjectors of the prior art require substantial effort from the user. For example, those automatic insertion systems may involve deflection of one or more flexible parts of the autoinjector, or they may imply overcoming a resisting force between two parts of the autoinjector, in such a way that the patient needs to apply a high force on the autoinjector at the time he wishes to activate the triggering means. The high force necessary for activating the triggering means may hurt the user. It may also cause the user to be reluctant to proceed to the injection, or to be puzzled, not knowing if he should continue the injection or not.

It is therefore important that at least the insertion of the needle into the injection site, which is the first step to take place in the injection process, be simplified and proceed softly and smoothly with no opportunity for the user to face anxiety. In this view, it is important that the user needs not apply too high a force on the device at the time he is ready to activate the triggering means for proceeding to the insertion step of the needle into the site of injection.

In addition, many autoinjectors of the prior art are designed so that the container, such as a syringe for example, is assembled into the device during the manufacture of the motor part, pieces of the motor part and of the container being connected together in an intricate way. Proceeding this way means that, once a motor part is designed for a syringe of a certain volume capacity and prefilled with a specified drug, it is not possible to use the same motor part for another type of container or for another drug, as it has been designed to fit with the specific shape of the syringe.

Nevertheless, for the pharmaceutical companies, it would be advantageous to prepare on one hand the prefilled syringe, and on the other hand the motor part of the autoinjector, and then assemble the prefilled syringe onto the motor part of the autoinjector, without having to redesign the motor part each time the type of syringe is changed or each time the drug is replaced by another drug with different properties, for example with a different viscosity.

Autoinjectors have been proposed, for which at least a part of the motor part is positioned laterally with respect to the syringe.

Nevertheless, such autoinjectors still need to be improved in particular with respect to the safety system intended to protect the needle at the end of injection, and to prevent access to said needle as soon as possible after the injection is completed. In this view, it is important to preserve the security of the user and that the needle be not accessible to the user, even in case of misuse of the device, for example by removing it from the injection site before the injection is completed.

In addition, as mentioned before, as users of these autoinjectors are usually not professional healthcare workers, it is desirable that such devices have a high reliability, and that not only the insertion step, but the whole process of the injection, from insertion of the needle into the injection site to withdrawal of the device from the injection site and disposal of the device proceeds softly and smoothly with no opportunity for the user to face anxiety.

A first aspect of the invention is a device for injection of a product into an injection site, said device comprising:

a housing having a longitudinal axis A and receiving a container for the product to be injected, said container being aligned on said longitudinal axis, said container being substantially closed at a proximal end by a stopper, said stopper being capable of being moved distally within said container so as to expel the product to be injected, and at a distal end by a needle for the exit of the product to be injected, said container being movable with respect to said housing between a first position, in which the needle does not extend beyond a distal end of the housing, and a second position, distally spaced with respect to said first position, in which the needle extends beyond the distal end of the housing, biasing means, coupled to said container and to said housing at least from said first position to said second position of the container, designed for exerting a distal force on said container so as to move said container from its first position to its second position when going from a first state to a second state, said second state being less stressed than said first state, retaining means coupled to said container and to said housing in the first position of the container, for releasably maintaining said biasing means in its first state, said retaining means being capable of moving from a passive condition, in which it maintains said biasing means in its first state, to an active condition, in which said biasing means is free to expand to its second state, triggering means capable of moving said retaining means from its passive condition to its active condition, wherein said retaining means comprise a lever member having a pivoting part rotatable around an axis R1 and at least a radial projection extending from said pivoting part, said radial projection being in a first angular position when said retaining means is in its passive condition, said radial projection being in a second angular position, different from said first angular position, when said retaining means is in its active condition, said axis R1 of said pivoting part being included in a transversal plane of said longitudinal axis A.

The arrangement of the device of the invention allows a patient to proceed to the insertion step of the needle with no substantial effort: indeed, as will appear from the description below, the retaining means of the device of the invention comprise a rotatable pivoting part that is included in a transversal plane of said longitudinal axis A. The release of these retaining means, and thereby the freeing of the biasing means intended to cause the insertion of the needle, imply a partial rotation of this pivoting part, this rotation being caused by cooperation of the triggering means with such pivoting part. Contrary to the autoinjectors of the prior art, thanks to the arrangement of this pivoting part in a transversal plane of the longitudinal axis of the container, the cooperation of the retaining means with the triggering means for freeing the biasing means require only little force. The user needs therefore not to apply the device of the invention with a high force on his skin at the time he wishes to activate the triggering means in order to initiate the insertion of the needle.

In particular, because of the arrangement of the retaining means of the device of the invention requiring little effort for initiating the insertion step, it is possible to provide the device of the invention with biasing means having an high force. Indeed, thanks to the arrangement of the retaining means of the device of the invention, the effort required for beginning the insertion step will remain the same regardless from the force of the biasing means. Moreover, in the embodiments in which the biasing means also serve for pushing distally the stopper, via a plunger rod or not, during the injection step, it is possible to provide the device with biasing means showing a high intrinsic force. For example, when the product to be injected shows a high viscosity, the device of the invention may be provided with biasing means having a high intrinsic force allowing said biasing means to automatically realize both the insertion step and the injection step, while the effort required from the user at the beginning of the process in order to initiate the insertion step remains low.

In embodiments, said biasing means is a spring linked to said stopper via a plunger rod, said device further comprising releasable maintaining means for maintaining said container fixed with respect to said plunger rod when said spring goes from its first state to its second state, said maintaining means being released when said spring reaches its second state. In embodiments, the spring is a concentric double helical spring: such a spring may show a high intrinsic force and may be used, for example, for completing both the insertion step and the injection step when the product to be injected shows a high viscosity.

In embodiments, said maintaining means comprise a hook fixed with respect to said container, said hook trapping a peg located on said plunger rod, the peg being allowed to escape from said hook under the force of the spring only once said container has reached its second position and said spring is in its second state.

Such embodiments enhance the safety of the device as they ensure the injection may not start before the needle is correctly inserted at the injection site.

In embodiments, the triggering means comprises a button mounted in pivoting relationship with respect to said housing, said button comprising a pushing surface accessible to a user for pivoting said button, said button further comprising an actuating surface capable of cooperating with said lever member for moving said radial projection from its first angular position to its second angular position, when the button is caused to pivot. For example, in its first angular position, the radial projection extends in an oblique or transversal direction with respect to the distal direction, and in its second angular position, the radial projection extends in the distal direction. The moving of the radial projection from its first angular position to its second angular position therefore benefits from the natural gravitational force and is completed with no high force required from the user.

In embodiments, the actuating surface comprises an edge of said button cooperating with said pivoting part of said lever member when the button is caused to pivot. Alternatively, the actuating surface may comprise a groove of said button cooperating with a peg of said radial projection of said lever member, when the button is caused to pivot.

In embodiments, the device further comprises:

locking means for preventing said triggering means from moving said retaining means from its passive condition to its active condition, said locking means being releasable, and deactivating means for releasing the locking means.

The device of the invention is therefore very safe as it cannot be triggered before having neutralized the security system formed by the releasable locking means.

In embodiments, the locking means comprise a movable surface of said device, said surface being movable between a first position, in which it prevents cooperation between said lever member and said button, to a second position, in which it allows cooperation between said lever member and said button, said movable surface being caused to move from its first position to its second position by said deactivating means.

In embodiments, said deactivating means being capable of going from a before use position, in which it does not release the locking means, to an active position in which it releases the locking means and the triggering means may be activated, the device further comprises storage elastic return means for urging said deactivating means back in its before use position as long as the triggering means have not been activated.

Such an embodiment allows the user to apply the device at another location on the skin after having already tried a first location and even released the locking means at this first location. As long as the triggering means have not been activated, the step of releasing the locking means is reversible.

In embodiments, the device further comprises:

fixing means for maintaining said container in its second position with respect to said housing, and urging means coupled to said stopper and to said housing when said container is in its second position, said urging means being designed for distally moving said stopper when going from a first state to a second state, said second state being less stressed than said first state, thereby realizing injection of the product.

The device of the invention is therefore entirely automated, as both the insertion step and the injection step are automatically completed by means of the biasing means and of the urging means. The user is therefore ensured that these two steps proceed optimally, as he does not have to manually complete them.

In embodiments, said spring being further capable of going from its second state to a third state, during which said spring moves the stopper distally, said third state being less stressed than said second state, said spring forms both said biasing means and said urging means.

Such an embodiment allows to manufacture a compact device as only one spring is required for automatically performing two steps, namely an insertion step, during which the needle is inserted into the injection site, and an injection step, during which the product to be injected is actually delivered to the injection site. As seen above, such a spring may be a concentric double helical spring having a high intrinsic force, adapted for completing the injection step of a viscous product.

In embodiments, the fixing means comprise a peg fixed with respect to said container and a window located on said housing, said peg being locked within said window when said container is in its second position with respect to said housing.

In embodiments, the device further comprises:

needle protection means, at least partially received within said housing, and movable with respect to said housing when said container is fixed in its second position with respect to said housing between an insertion position, in which a distal tip of the needle extends beyond the distal end of the needle protection means, and a final position, in which the distal tip of the needle does not extend beyond the distal end of the needle protection means, and elastic return means, coupled to said needle protection means and to said container, and designed for automatically moving said needle protection means from its insertion position to its final position, upon removal of the device from an injection site by a user.

The device of the invention therefore requires no particular effort from the user, is of simple use and perfectly safe: once the needle has been inserted into the injection site, as soon as the user withdraws the device from the injection site, the needle protection is triggered, and the needle is immediately rendered inaccessible to the user. In addition, in case the user misuses the device and withdraws it from the injection site before the injection is actually completed, the needle protection is nevertheless triggered. Actually, as soon as the needle is inserted in the injection site, the removal of the device from the injection will automatically trigger the needle protection. The device of the invention is therefore very comfortable for the user, in particular where the user is not a professional healthcare worker, as the user knows the used needle will never come in contact with his hand or fingers, regardless of how he performs the injection step.

In embodiments, in the first position of the container with respect to the housing, said needle protection means being movable with respect to said housing between a before use position and a use position, said use position being proximally spaced with respect to said before use position, at least part of said needle protection means forms said deactivating means.

The device of the invention is therefore easy to use, as it simply requires that the user applies the device on the skin of the patient and moves the housing with respect to the needle protection means in order to release the locking means.

In embodiments, said biasing means being positioned so as to produce a distal force along an axis parallel to said longitudinal axis A, said device further comprises a linking member coupled to said biasing means and to said container, said linking member being shaped and dimensioned so as to transmit said distal force to said container. By "axis parallel to the longitudinal axis A" is meant in the present application, an axis having the same direction as the longitudinal axis A, in other words, oriented along the distal-proximal direction, but separate, for example laterally spaced, from said longitudinal axis A. As will appear later in the description, such a location of the biasing means allows the device of the invention to be manufactured in two steps.

For example, a motor part of the device, comprising the biasing means, the retaining means, the triggering means and the urging means may be assembled on one hand. On another hand, the housing part may be assembled separately, said housing part comprising the housing, the deactivating means, the fixing means, the needle protection means and the elastic return means. The locking means may alternatively be part either of the motor part or of the housing part. Each part, namely the motor part on one hand and the housing part on the other hand, is autonomous before it is connected to the other part, and may be transported and/or handled on its own. This allows pharmaceutical companies for example to prefill the container, for example a syringe, of the housing with the drug to be injected on a first site, and then to assemble the motor part later on. In particular, thanks to the arrangement of the device of the invention, it is not necessary to redesign the motor part each time the type of syringe is changed or each time the drug is replaced by another drug with different properties, for example with a different viscosity.

In embodiments, said plunger rod forms said linking member, said plunger rod comprising a shaft aligned on said longitudinal axis A, said shaft being provided at its distal end with said stopper, a bridge linking a proximal end of said shaft to a proximal end of a lateral tubular lodging parallel to said longitudinal axis A and receiving said spring, said spring being in distal abutment on a distal transversal wall of said tubular lodging and being in proximal abutment on a proximal transversal wall fixed with respect to said housing. For example, the bridge extends in a radial direction with respect to the longitudinal axis A and the lateral tubular lodging has a longitudinal axis which parallel to the longitudinal axis A. The plunger rod may therefore have a global U-shape.

In embodiments, the device of the invention is under the form of two autonomous connectable parts, namely a motor part and a housing part, said motor part comprising at least said biasing means, said retaining means, said triggering means, and said urging means, said housing part comprising at least said housing, said deactivating means, said fixing means, said needle protection means and said elastic return means, said locking means being located on one of said motor part and housing part said device further comprising connecting means for connecting said motor part to said housing part at time of use.

As seen above, the arrangement of the various parts of the device of the invention, and in particular the fact that the biasing means and the urging means are located laterally with respect to the longitudinal axis of the housing, allow to treat, transport, and/or handle the motor part on one hand, and the housing part on the other hand, before connecting these two parts. This is advantageous for pharmaceutical companies which fill the container of the housing independently from the motor part. In addition, thanks to the arrangement of the device of the invention allowing said device to be under the form of two connectable parts, it is not necessary to redesign the motor part each time the type of syringe/container is changed or each time the drug is replaced by another drug with different properties.

Figure 1D:
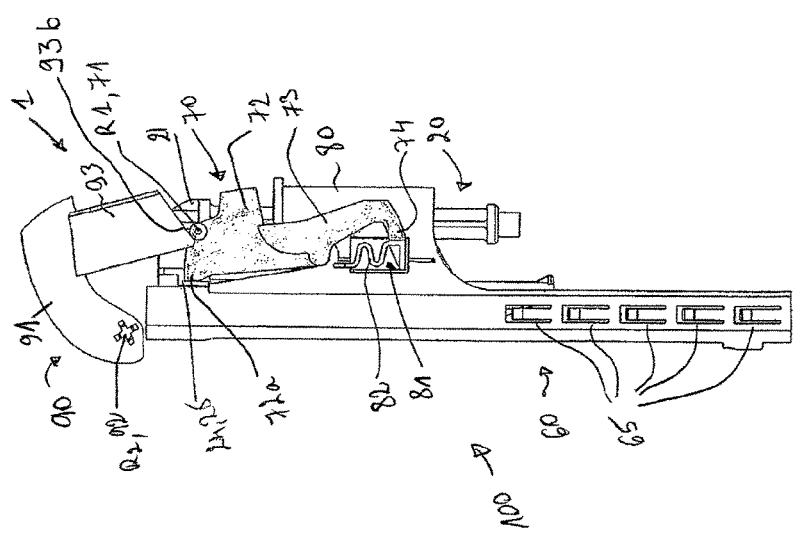
Figure 6:
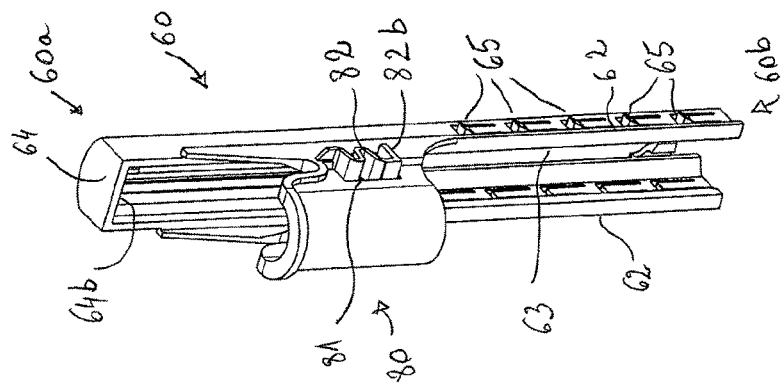
Figure 5:
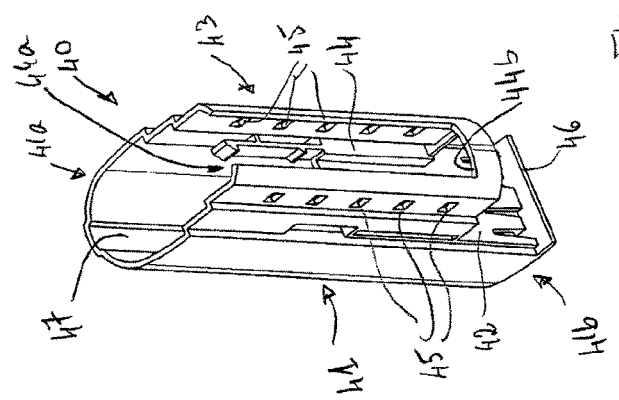
Figure 4:
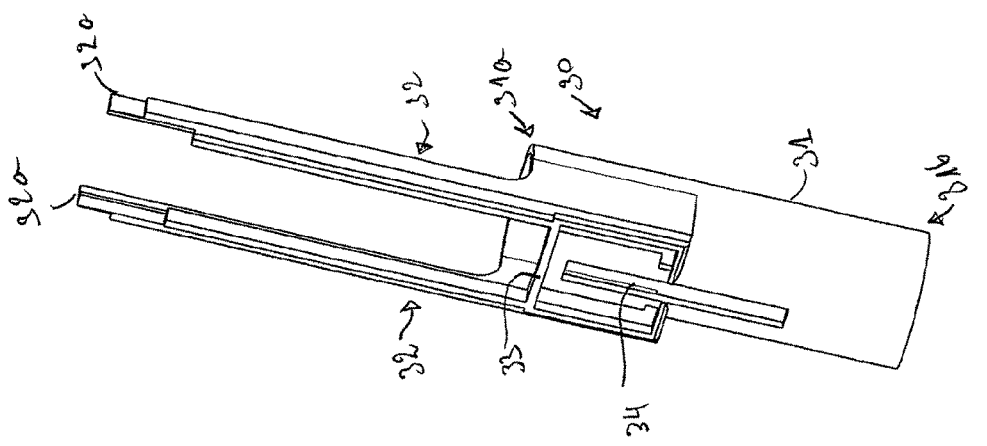
Figure 7:
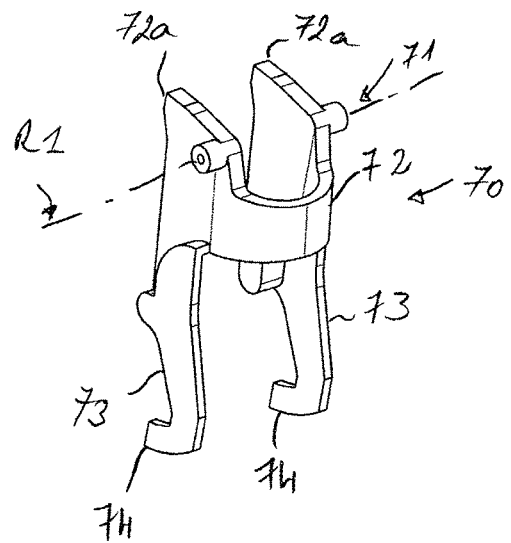
Figure 8:
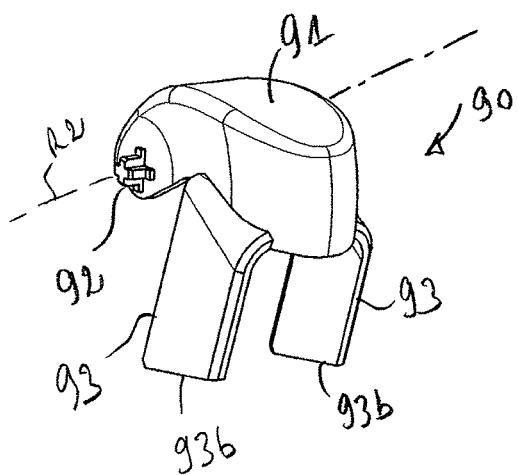
Figure 11:
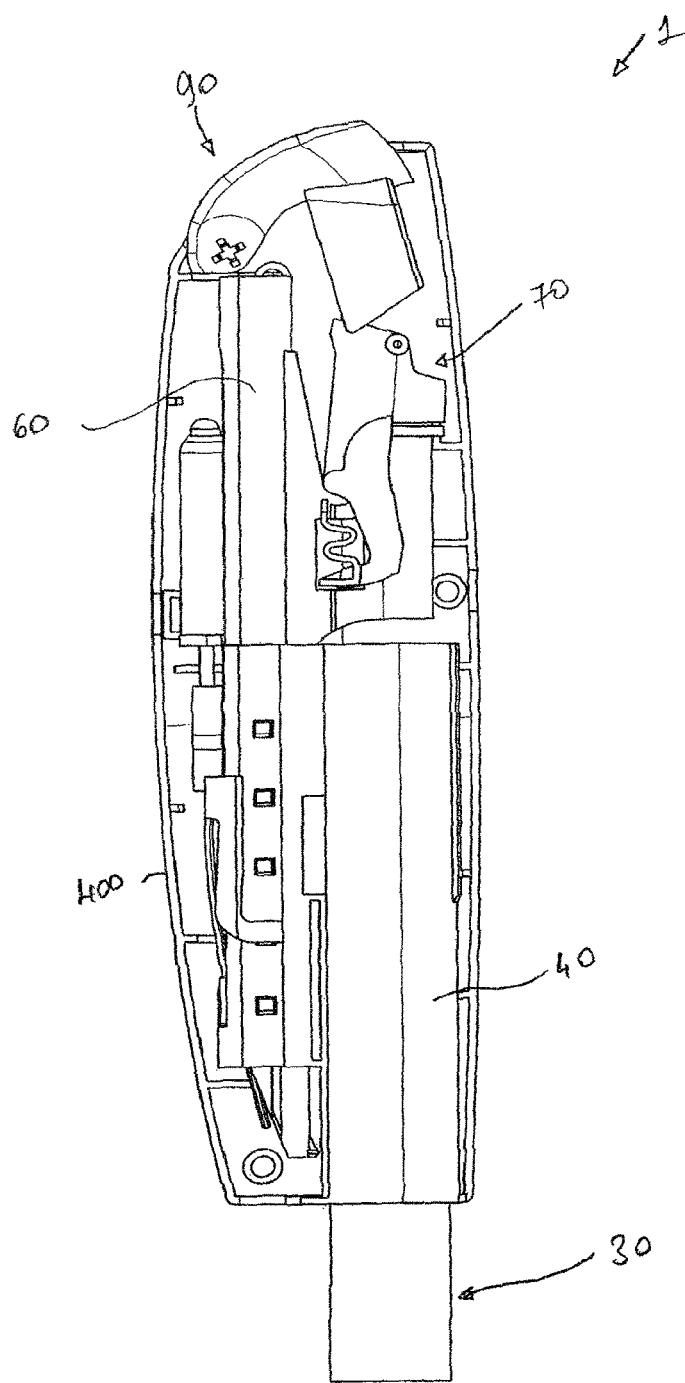
Figure 12C:
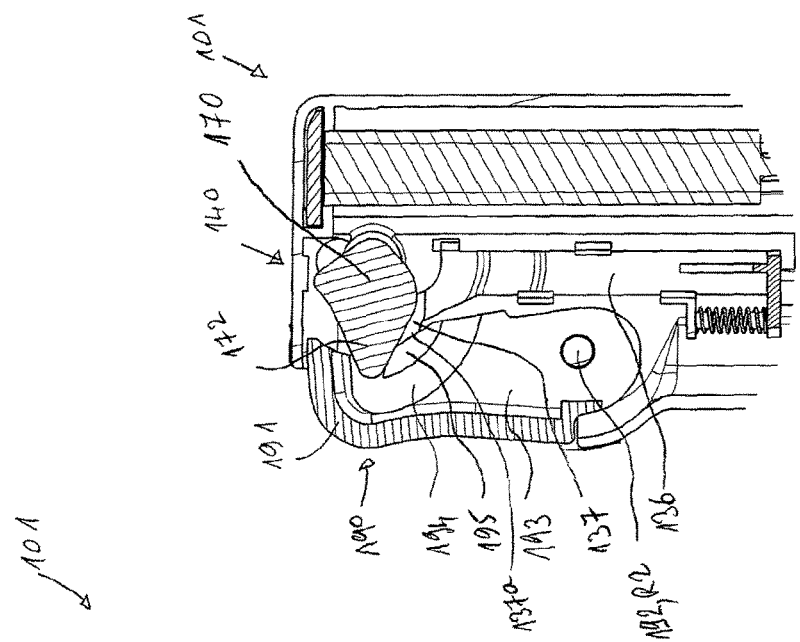
Figure 12B:
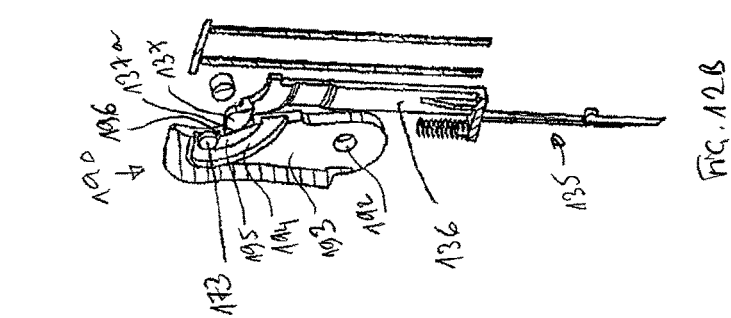
Figure 12A:
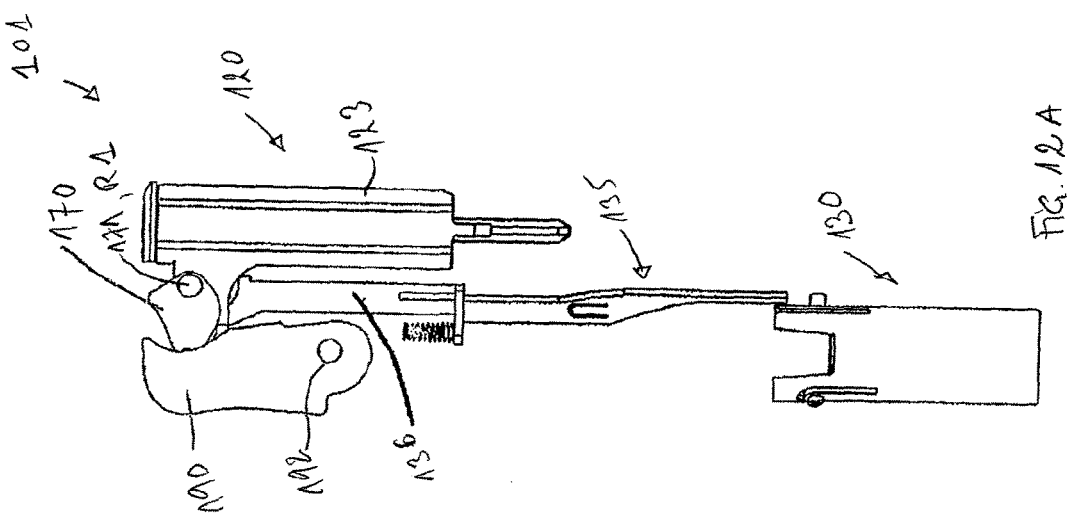
Figure 14:
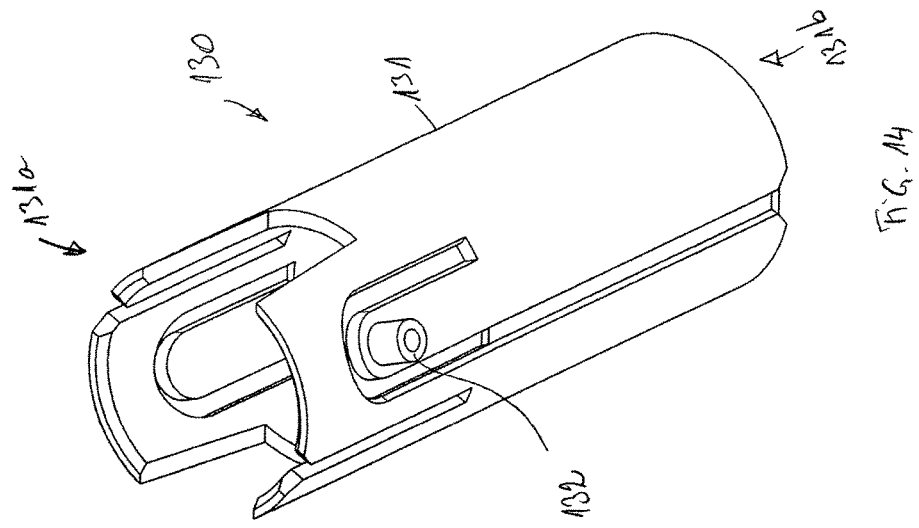
Figure 13:
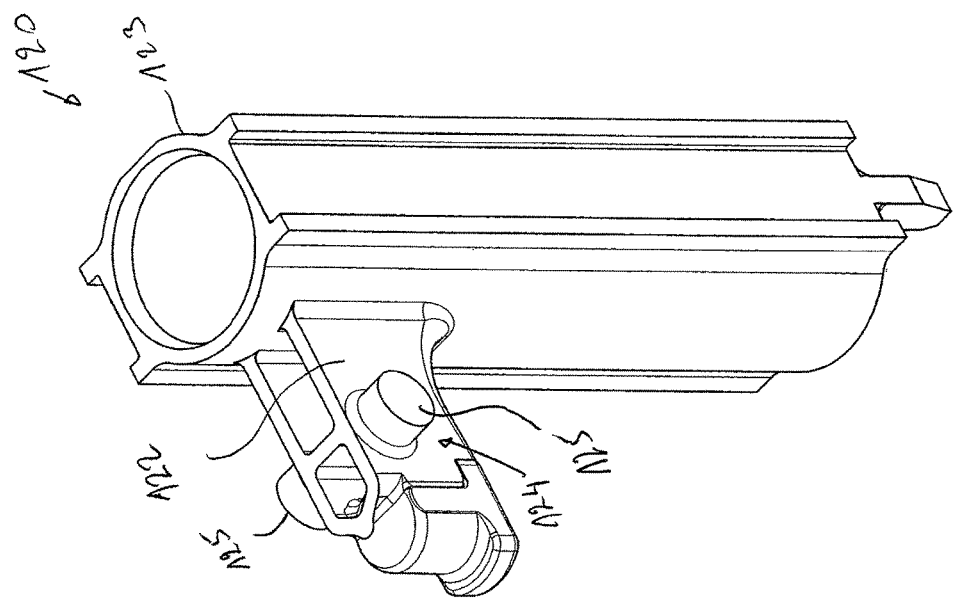
Figure 16B:
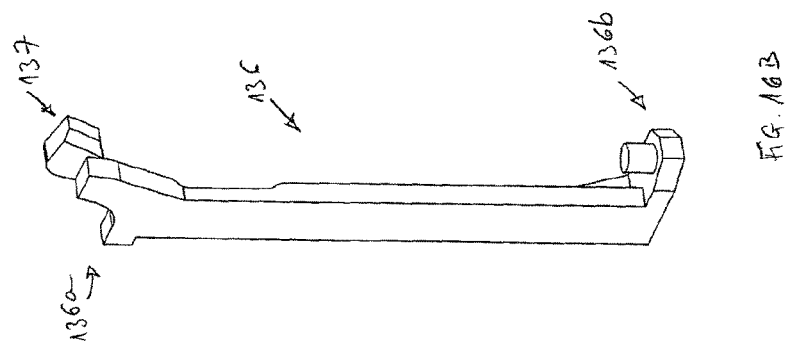
Figure 16A:
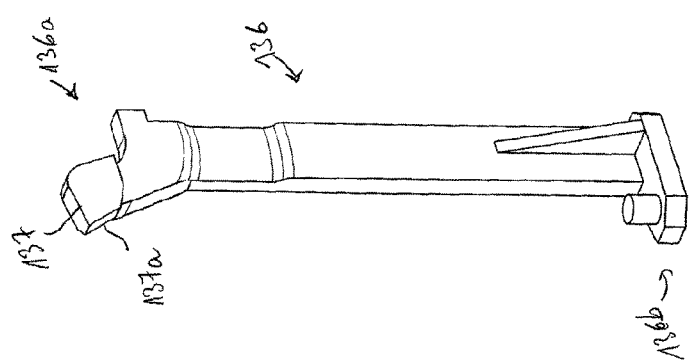
Figure 15:
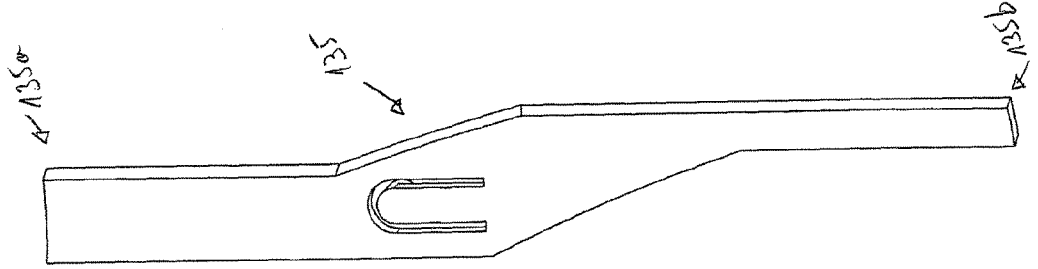
Figure 17:
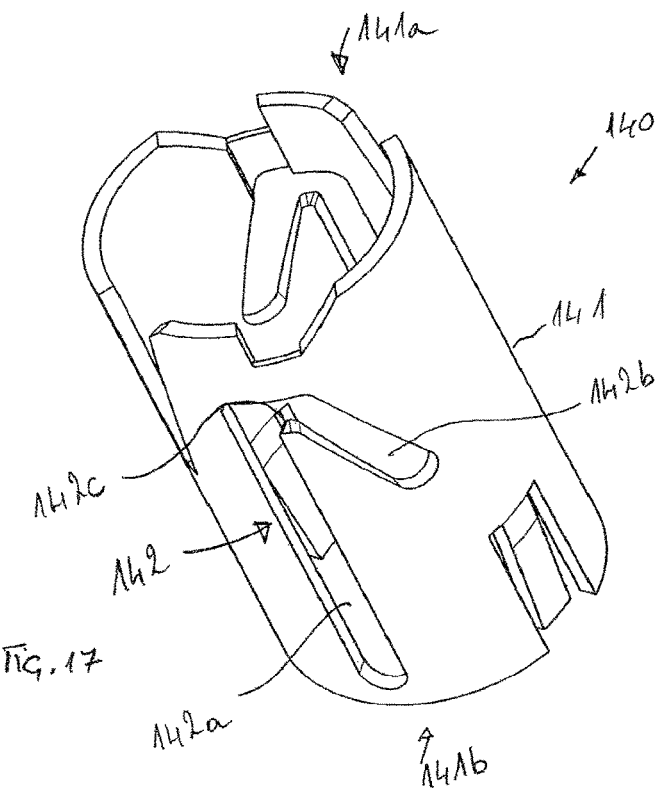
Figure 18:
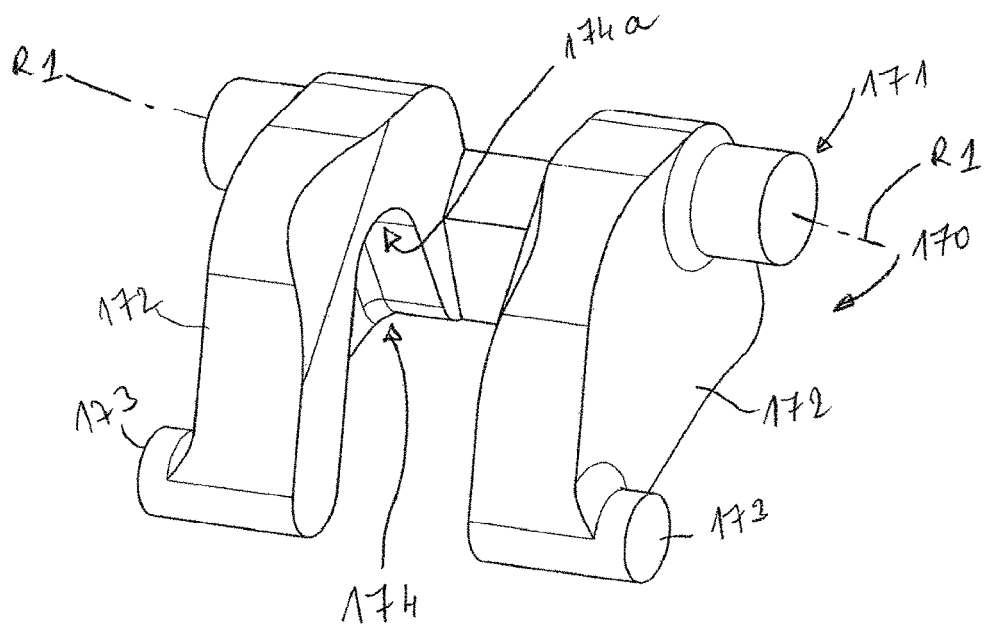
Figure 22A:
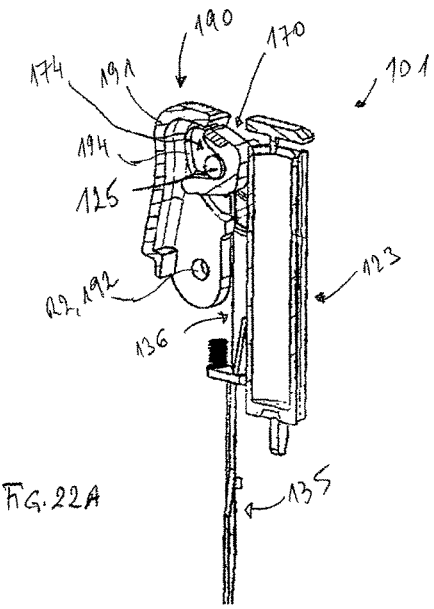
Figure 22B:
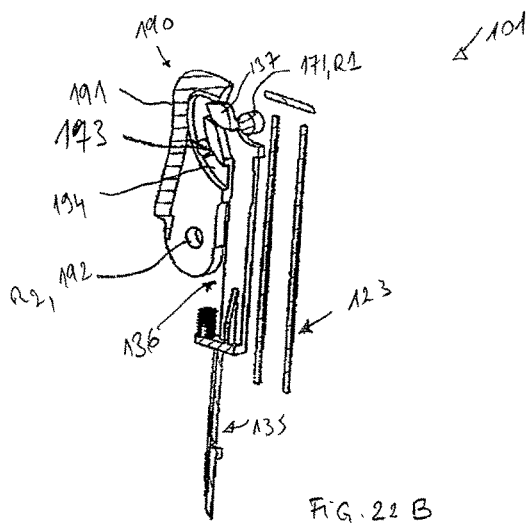
Figure 23A:
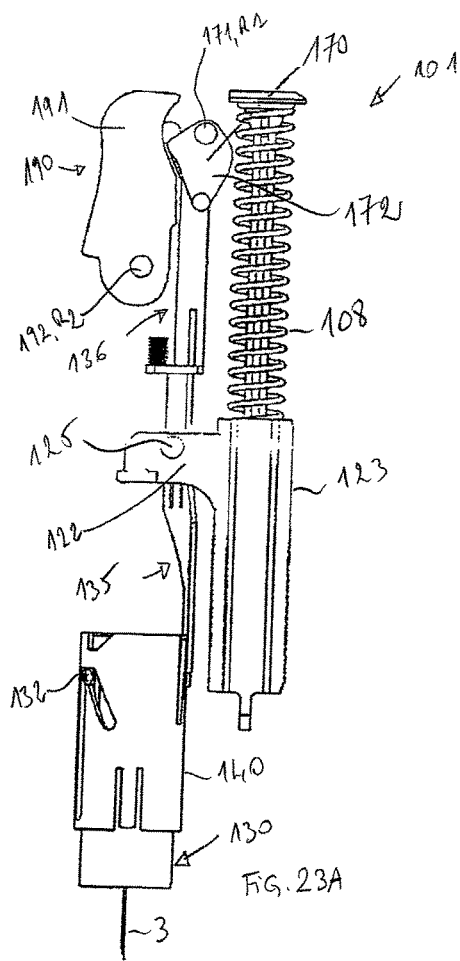
Figure 23B:
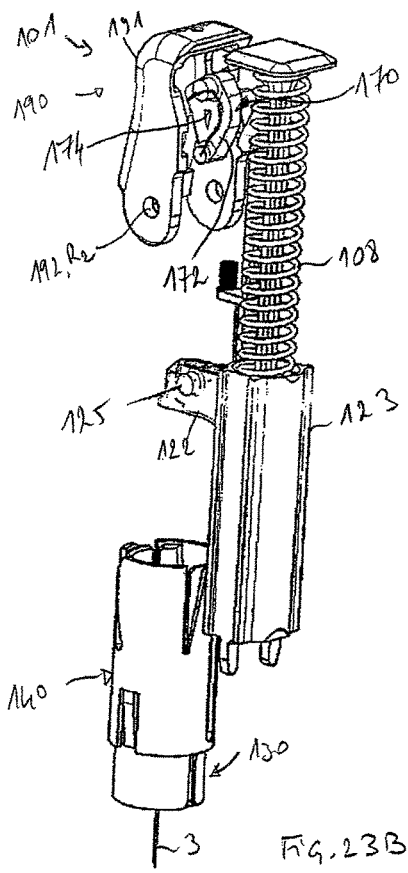
Figure 24:
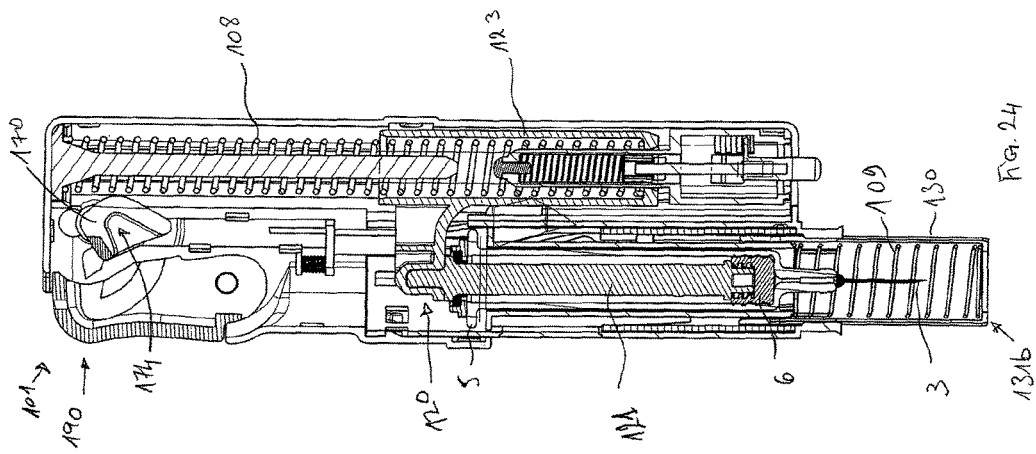
Figure 23C:
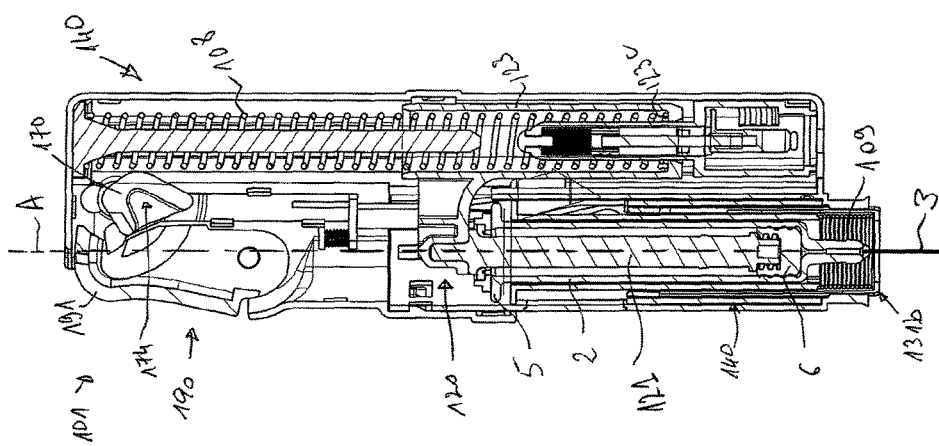

The present invention will now be described in greater detail based on the following description and the appended drawings in which:

FIGS. 1A-1C are respectively a side view, a cross section view, and a perspective view of the device of the invention in a before use position, FIGS. 1D-1E are two partial side views of the device of FIGS. 1A-1C, respectively of the motor part of the device of FIG. 1A, and of the motor part with the needle protection sleeve, FIGS. 2A-B are views of the syringe holder of the device of FIG. 1A, respectively a perspective view and a side view, FIGS. 3A-3B are views of the plunger rod of the device of FIG. 1A, respectively a perspective view from the bottom and a perspective view from the top, FIG. 4 is a perspective view of the needle protection sleeve of the device of FIG. 1A, FIG. 5 is a perspective view of the housing of the device of FIG. 1A, FIG. 6 is a perspective view of the support of the device of FIG. 1A, FIG. 7 is a perspective view of the lever member of the device of FIG. 1A, FIG. 8 is a perspective view of the button of the device of FIG. 1A, FIGS. 9A-9B are views of the device of FIG. 1A, in a position where the deactivating means have released the locking means, and the retaining means are in their active condition, respectively a side view and a partial cross section view, FIG. 10A-10B are views of the device of FIG. 1A once the triggering means have been activated, respectively a side view and a partial cross section view, FIG. 11 is a side view of the device of FIG. 1A after the needle protection means has reached its final position, FIGS. 12A and 12B are partial side view and perspective view of an alternative embodiment of the device of the invention, FIG. 12C is a partial cross section view of the device of FIGS. 12A and 12B, FIG. 13 is a perspective view of a part of the plunger rod of device of FIGS. 12A and 12B, FIG. 14 is a perspective view of the needle protection sleeve of the device of FIGS. 12A and 12B, FIG. 15 is a perspective view of a part of the deactivating means of the device of FIGS. 12A and 12B, FIGS. 16A and 16B are perspective views of a part of the deactivating means of the device of FIGS. 12A and 12B, FIG. 17 is a perspective view of a part of the housing of the device of FIGS. 12A and 12B, FIG. 18 is a perspective view of the lever member of the device of FIGS. 12A and 12B, FIGS. 19A and 19B are two perspective views of the button of the device of FIGS. 12A and 12B, FIGS. 20A and 20B are partial perspective and cross section views of the device of FIGS. 12A and 12B during the deactivation of the locking means, FIGS. 21A and 21B are partial side and perspective views of the device of FIGS. 12A and 12B showing activation of the triggering means, FIGS. 22A and 22B are partial perspective views of the device of FIGS. 12A and 12B showing the retaining means going from its passive condition to its active condition, FIGS. 23A, 23B and 23C are partial side and perspective views and cross section view of the device of FIGS. 12A and 12B during the insertion step, FIG. 24 is a cross section view of the device of FIGS. 12A and 12B in a final position, after activation of the needle protection means.

With reference to FIGS. 1A-1E, is shown a device 1 of the invention comprising:
- a syringe 2 comprising a needle 3, a flange 5, a stopper 6, filled with a product 7,
- a syringe holder 10,
- a plunger rod 20,
- a needle protection sleeve 30,
- a housing 40,
- a support 60,
- a lever member 70,
- a button 90,
- a concentric double helical spring 8,
- a simple helical spring 9

With reference to FIGS. 1A-11, the different parts of the device 1 will now be described in details.

With reference to FIGS. 2A-2B, the syringe holder 10 has the global shape of a tube. It is shaped and dimensioned so as to be able to receive the syringe 2 with the flange 5 of the syringe 2 bearing onto a proximal rim 11 of the syringe holder 10. The syringe holder 10 is provided on its outer wall with a ridge 12 extending from the proximal rim 11 in the distal direction and terminated by a peg 12a. The outer wall of the syringe holder 10 is further provided with a flexible hook 13 extending radially outwardly, this hook 13 being substantially diametrically opposed to the peg 12a in the example shown. The hook 13 is provided with snap-fitting means allowing the hook 13 to act as a jaw, as will appear from the description below. Distally spaced from the hook 13, a radially flexible outer peg 14 is present on the outer wall of the syringe holder 10. The syringe holder 10 is further provided with a distal inner rim 15.

With reference to FIGS. 3A-3B, the plunger rod 20 comprises a shaft 21 having a proximal end 21a and a distal end 21b. As will appear from the description below, the shaft 21 is dimensioned so as to be able to be received within the syringe 2, and its distal end 21b is free and is intended to be coupled to the stopper 6 of the syringe 2. At its proximal end 21a, the shaft 21 is provided with a bridge 22 linking the shaft 21 to a longitudinal tubular lodging 23 open at its proximal end 23a and at its distal end 23b. The longitudinal axis of the shaft 21 and the longitudinal axis of the longitudinal tubular lodging 23 are parallel and the plunger rod 20 has a global U-shape. On each of its outer side walls, the bridge 22 is provided with an outer relief 24 forming a proximal abutment 25. On its outer wall facing the shaft 21, the longitudinal tubular lodging 23 is provided at its distal end with an outer radial peg 26.

With reference to FIG. 4, the needle protection sleeve 30 is dimensioned and shaped so as to be able to receive the syringe holder 10. The needle protection sleeve 30 comprises a distal sleeve 31 having a proximal end 31a and a distal end 31b and a globally tubular shape. At its proximal end 31a, the distal sleeve 31 is provided with two lateral walls 32, parallel to each other and extending in the proximal direction, each having a proximal face 32a. The two lateral walls 32 are linked to each other by a bridging wall 33. The bridging wall 33 is provided with a longitudinal window 34.

With reference to FIG. 5, the housing 40 has the global shape of a tube 41 open at its proximal end 41a and its distal end 41b, provided in its distal region with an intermediate back wall 42 having a planar shape. Backwards from the intermediate back wall 42 is provided an additional lodging 43 provided with a longitudinal window 44 open at its proximal end 44*a* and having a distal edge 44*b*. The housing 40 is dimensioned and shaped so as to be able to receive the needle protection sleeve 30, the syringe holder 10 and the syringe 2. As will appear from the description below, the lodging 43 will be useful for assembling the housing 40 to the other main part of the device 1, namely the motor part 100 (see FIG. 1D).

Each lateral wall of the lodging 43 is provided on the example shown with a series of recesses 45 distributed longitudinally and intended to be part of the connecting means for assembling the housing 40 to the motor part 100 (FIG. 1D) of the device 1. At its distal end 41*b*, the tube 41 is provided with an outer radial rim 46. The housing 40 is further provided on its inner wall opposite the intermediate back wall 42 with a proximal longitudinal groove 47.

With reference to FIG. 6, the support 60 has the global shape of a longitudinal cage open on one side and at the bottom. The cage therefore comprises three longitudinal walls, two lateral walls 62 and a back wall 63 bridging together the two lateral walls 62. For purposes of description of the support 60, the back is designated as being the wall bridging the two lateral walls, and the front is designated as being opposite the back. At its proximal end 60*a*, the support 60 comprises a top wall 64 having a distal face 64*b*. At its distal end 60*b*, the support 60 is open. Each lateral wall 62 is provided in its distal region with a series of outer pegs 65 distributed longitudinally and intended to be part of the connecting means for assembling the support 60 (which is part of the motor part 100 of the device 1 as shown on FIG. 1D) with the housing 40 of the device 1. As shown below, the outer pegs 65 are intended to cooperate with the recesses 45 of the housing 40 for connecting the housing 40 to the motor part 100 of the device 1.

In its middle region, the support 60 is provided with a semi-tubular element 80 extending in the front direction: this semi-tubular element 80 is dimensioned and shaped so as to be capable of surrounding the shaft 21 of the plunger rod 20. The semi-tubular element 80 is provided with two lateral and opposite windows 81: in each lateral window 81, is lodged a longitudinal spring element 82, capable of going from an expanded state (as shown on FIG. 6), to a compressed state (see FIG. 9A) when submitted to a proximal force.

With reference to FIG. 7, the lever member 70 comprises a pivoting part 71 rotatable around an axis R1. The pivoting part 71 is provided with a U-shaped element 72, the free ends of the U being provided with end projections 72*a*. The U-shaped element 72 is dimensioned and shaped so as to be capable of surrounding the shaft 21 of the plunger rod 20. The lever member 70 is further provided with two parallel legs 73 extending from the pivoting part 71 in the radial direction with respect to axis R1. Each radial leg 73 is provided at its free end with a peg 74. As will appear from the description below, as the pivoting part 71 rotates around its longitudinal axis R1, the legs 73 describe a circle and are capable of changing angular positions.

With reference to FIG. 8, the button 90 has the global shape of a cap 91: the cap 91 is provided with a pivoting part 92 rotatable around an axis R2. The cap 91 is further provided with two parallel longitudinal lateral walls 93 extending in a radial direction with respect to axis R2. Each lateral wall 93 has a globally rectangular shape with a distal edge 93*b*.

The operation of the device 1 of the invention will now be explained with reference to FIGS. 1A-11.

With reference to FIG. 1D is shown what is called the motor part 100 of the device 1, namely the plunger rod 20, the support 60, the lever member 70, the button 90. Although not visible on FIG. 1D, the concentric double helical spring 8 is also part of the motor part 100.

As appears from FIGS. 1A-1E, in which the device 1 is in a before use position, the support 60 and the plunger rod 20 are coupled together via the concentric double helical spring 8 and the lever member 70. The concentric double helical spring 8 is received within the longitudinal tubular lodging 23. The longitudinal tubular lodging 23 is lodged within the proximal region of the inner space of the support 60. The distal end of the double helical spring 8 bears on the proximal face of an inner distal rim 23*c* of the longitudinal tubular lodging 23, and the proximal end of the double helical spring 8 bears on the distal face 64*b* of the top wall 64 of the support 60. The concentric double helical spring 8 is therefore aligned on the longitudinal axis of the longitudinal tubular lodging 23 of the plunger rod 20.

In the before use position of the motor part of the device as shown on FIGS. 1A-1E, the concentric double helical spring 8 is in a first state, which is a stressed state. As such, the concentric double helical spring 8 naturally tends to separate the plunger rod 20 from the support 60. Nevertheless, the lever member 70 acts as retaining means for maintaining the concentric double helical spring 8 in its first stressed state. Indeed, as shown on FIGS. 1D-E, the end projections 72*a* of the lever member 70 are engaged in the proximal abutments 25 of the bridge 22 of the plunger rod 20, and the pegs 74 of the radial legs 73 of the lever member 70 are in abutment against the spring element 82 of the support 60. In this position, the spring element 82 is in an expanded state, which is its rest state, and the lever member 70 is not allowed to rotate around its axis R1. In addition, as shown on FIGS. 1A-1E, the lever member 70 is positioned so as to have its rotatable pivoting part 71 included in a plane that is transversal with respect to the longitudinal axis of the longitudinal tubular lodging 23 of the plunger rod 20.

As shown also on FIG. 1D, the semi-tubular element 80 of the support 60 and the U-shaped element 72 of the lever member 70 both surround the shaft 21 of the plunger rod 20.

As further shown on FIG. 1D, the motor part 100 of the device further comprises the button 90 which is pivotingly mounted on the support 60. The distal edge 93*b* of the lateral walls 93 are in abutment onto the axis R1 of the pivoting part 71 of the lever member 70. As a consequence, since the lever member 70 is in this position blocked in rotation, the button 90 is also blocked in rotation. As a consequence, pushing distally on the cap 91 of the button 90 for making it pivot around axis R2 will be unsuccessful.

As shown on FIG. 1D, the motor part 100 is an autonomous part of the device 1 of FIGS. 1A-1E, that may be transported and/or handled on its own. This motor part 100 is intended to be connected to the housing part of the device, said housing part comprising the housing 40 containing the prefilled syringe 2, as will appear from the description below. In this view, the motor part 100 comprises means for connecting the support 60 to the housing 40, under the form of the pegs 65.

With reference to FIGS. 1A-1C, the motor part 100 of FIG. 1D has been connected to the housing part for forming the device 1 of the invention. The motor part 100 is connected to the housing 40 of the housing part by means of the pegs 65 of the support 60 being snap-fitted within the corresponding recesses 45 of the housing 40. As such, all the elements of the motor part which were previously described as being coupled to the support 60 are therefore now coupled to the housing 40 itself, via said support. In the same way, the elements of the motor part which were previously described as being pivotingly mounted with respect to the support 60, such as the button 90, are now pivotingly mounted with respect to the housing 40.

With reference to FIGS. 1A-1C, the arrangement between the various elements received within the housing 40, and therefore forming the housing part of the device 1, will now be described. The housing 40 has a longitudinal axis A (see FIG. 1B), aligned on the proximal-distal direction and on the longitudinal axis of the syringe 2.

A first element contained in the housing 40 is a container, having the form of a syringe 2 in the example shown, aligned on the longitudinal axis A. The syringe 2 has a global tubular shape and is substantially closed at its distal end by a needle 3 for the exit of the product to be injected. As shown on FIG. 1A, the syringe 2 is prefilled with the product 7 to be injected and is closed at its proximal end by a stopper 6. As will appear in the following description, the stopper 6 is capable of moving within the syringe 2 under distal pressure and is intended to cooperate with the distal end of the shaft 21 of the plunger rod 20 in order to realize injection of the product 7. The syringe 2 is further provided at its proximal end with an outer flange 5.

The prefilled syringe 2 is received within the syringe holder 10 with the distal face of its outer flange 5 bearing onto the proximal rim 11 (see FIG. 2A) of the syringe holder 10. The syringe holder 10 is also aligned on longitudinal axis A and the syringe 2 is therefore blocked in distal translation with respect to the syringe holder 10. In addition, the syringe is further blocked in proximal translation with respect to the syringe holder 10 by means of friction force existing between the syringe 2 and the syringe holder 10. As a consequence, all elements herein described as being coupled to the syringe holder 10 are therefore also coupled to the syringe 2.

In the before use position of the device 1 as shown on FIGS. 1A-1C, the distal region of the syringe holder 10 is received in the needle protection sleeve 30. The needle protection sleeve 30 is aligned on longitudinal axis A of the syringe 2. The syringe holder 10 is coupled to the needle protection sleeve 30 by means of a helical spring 9, which is in a first stressed state, so that the distal end of helical spring 9 bears on a proximal face of an inner radial rim 36 of the distal sleeve 31 of the needle protection sleeve 30, while the proximal end of the helical spring 9 bears on the distal face of the distal rim 15 of the syringe holder 10. The helical spring 9 being in a first stressed state, it tends to separate the syringe holder 10 from the needle protection sleeve 30: as such, the syringe holder 10 and the needle protection sleeve 30 are further coupled together by means of radial outer peg 14 present on the syringe holder 10, this radial outer peg 14 being in proximal abutment against a proximal edge of longitudinal window 34 of the bridging wall 33 of the needle protection sleeve 30. As such, the radial outer peg 14 and the proximal edge of longitudinal window 34 act as means for maintaining the helical spring 9 in its first stressed state.

As shown on FIGS. 1A-1C, the syringe holder 10 and the needle protection sleeve 30 are further received within the housing 40, the syringe holder 10 being slidingly mounted on the housing 40 by means of the peg 12a of ridge 12 being engaged in the proximal longitudinal groove 47 of the housing 40.

In the before use position of the device 1 as shown on FIG. 1A, the syringe holder 10 is further connected to the motor part 100 of the device 1 by means of outer radial peg 26 of the plunger rod 20 being engaged in flexible hook 13 of the syringe holder 10.

Regarding the motor part 100, the arrangement and positions of its various elements in FIGS. 1A-1C are the same than the ones already described for FIG. 1D and are not repeated here again.

In particular, in the position of FIGS. 1A-1C, the lever member 70 is positioned so as to have its rotatable pivoting part 71 included in a plane transversal to the longitudinal axis A of the syringe 2. The radial legs 73 have an angular position such that said radial legs 73 extends in an oblique direction, offset from the longitudinal direction, from the pivoting part 71.

Moreover, in this position of FIGS. 1A-1C, the shaft 21 of the plunger rod 20, coupled to the stopper 6 via its distal end, is aligned on the longitudinal axis A of the syringe 2. As a consequence, the concentric double helical spring 8, which is lodged in the tubular lodging 23 of the plunger rod 20, is aligned on the longitudinal axis of the tubular lodging 23, which is parallel but separate from the longitudinal axis A. As will appear later in the description, this lateral position of the concentric double helical spring 8 with respect to the longitudinal axis A will allow the concentric double helical spring 8 to produce a distal force parallel to the longitudinal axis A when said concentric double helical spring 8 is freed. In the position of the device 1 shown on FIGS. 1A-1C, the housing 40 is fixed with respect to the support 60.

Although the housing 40, and the various elements it contains, namely the syringe 2, the syringe holder 10, the needle protection sleeve 30, has been described above in a position where it is connected to the motor part 100 of the device 1, such housing 40 and its elements form an autonomous part of the device 1 that may be transported and/or handled on its own.

The device 1 of the invention has therefore advantages for the pharmaceutical companies, which may fill the syringe 2 on a first site, and assemble the syringe 2 in the housing 40 on this first site, while the motor part 100 of the device 1 may be assembled on a second site. The motor part 100 and the housing 40 may then be connected to each other so as to obtain the device 1.

The device 1 of the invention is provided to the user in the configuration shown on FIGS. 1A-1C, preferably surrounded by an outer shell 400, as shown on these Figures. The user is usually a patient that will complete the injection on his own. When the user is ready, he grasps the device 1 of FIGS. 1A-1C for example by the shell 400.

The device 1 may not be triggered as long as the device 1 is not applied in a proper way on the skin of the patient.

FIG. 1E is a partial detail side view illustrating the relationship between the support 60 and the lever member 70 in the position of the device 1 before it has been applied on the skin of the patient. For clarity's sake, only the needle protection sleeve 30 of the housing part 40 is shown on FIG. 1E: in this position of the device 1, the pivoting part 71 of the lever member 70 is not allowed to rotate around its axis R1 because of the pegs 74 being in abutment against the spring element 82 of the support 60 in its expanded state.

As explained above, in this configuration, the lever member 70 acts as retaining means for maintaining the concentric double helical spring 8 in its first stressed state, and the lever member 70 is in a passive condition, as activation of the button 90 has no effect on the lever member 70 and therefore neither triggers the needle insertion step nor the injection of the product 7. The spring element 82 in its expanded state acts as locking means for preventing the triggering means (button 90 and its edge 93b) from moving the lever member 70 from its passive condition to its active condition.

With reference to FIG. 1E, one can see that, in this passive condition of the lever member 70, the proximal face 32a of each lateral wall 32 of the needle protection sleeve 30 faces directly the distal end 82b of spring element 82.

As a consequence, for allowing the lever member 70 to be able to go from its passive condition to an active condition, in which the insertion of the needle may be triggered, the user needs to apply the device 1 on his skin 10 or on the skin 10 of the patient via the distal end 31b of the distal sleeve 31 of the needle protection sleeve 30 as shown on FIGS. 9A-9B, and then push distally on the shell 400 which is fixed with respect to the housing 40. Because of the relationship described above between the housing 40 and the needle protection sleeve 30, this movement causes the needle protection sleeve 30 to move proximally with respect to the housing 40, and therefore with respect to the support 60, which is fixed with respect to the housing 40. While the needle protection sleeve 30 moves proximally with respect to the support 60, the proximal faces 32a of its lateral walls 32 push proximally onto the distal ends 82b of the spring elements 82.

As a consequence, and with reference to FIG. 9A, as its distal end 82b is pushed in the proximal direction by the proximal faces 32a of the needle protection sleeve 30, each spring element 82 is compressed and no more faces the peg 74 of the lever member 70. The locking means has therefore been released and pivoting movement of the button 90 is now possible allowing rotation of the pivoting part 71 of the lever member 70, as will appear later from description of FIG. 10A. During this step, the proximal faces 32a of the lateral walls 32 of the needle protection sleeve 30 form deactivating means of distal end 82b of spring element 82, acting as locking means for preventing the triggering means from moving the retaining means, namely the lever member 70, from its passive condition to its active condition. Moreover, with reference to FIG. 9B, the proximal movement of the needle protection sleeve 30 with respect to the syringe holder 10 has caused the helical spring 9 to be compressed. In addition, the spring element 82 allows the deactivating means, namely the needle protection sleeve 30, to come back to its storage position in case the user is not satisfied by the location where he has applied the device 1 on the skin in the first place and decides to remove the device 1 from the skin in order to apply it at another location before triggering injection. When the user removes the device 1 from the first location, the spring element 82 comes back to its rest and expanded state automatically, thereby locking again the triggering means, as far as those triggering means have not been activated yet. The spring elements 82 therefore act as storage elastic return means for urging the needle protection sleeve 30 back in its before use position, in the absence of any pressure applied on said housing 40 or needle protection sleeve 30.

The device 1 of the invention is therefore safe, as the user is allowed to give more than just one try in order to choose the appropriate location on the skin where he wishes to trigger the injection.

Once the user is satisfied with the location on the skin where he has applied the device 1, and once the locking means are released, as explained above, the user pushes distally on the cap 91 of the button 90. The button 90 being pivotingly mounted onto the support 60, the lateral walls 93 of the button 90 pivot and their edges 93b act upon the axis R1 of the lever member 70 so as to rotate its pivoting part 71. Only little force is required from the user for pushing cap 91 as the user may benefit from natural gravitational force for completing this step, the button 90 being pivotingly mounted onto the support 60 along a direction parallel to said longitudinal axis A. Because only low force is required from the user to perform this step, the device 1 may be used by people having difficulties for handling objects in their hands.

The radial legs 73 move from their first angular position (extending in an oblique direction) to their second angular position, in which they extend parallel to the distal direction, as shown on FIG. 10A. As a consequence of the radial legs 73 reaching their second angular position, the end projections 72a of the U-shaped element 72 of the lever member 70 escape the proximal abutment surface 25 of the relief 24 of the plunger rod 20 (see FIGS. 1D and 1E). While pressing distally onto the cap 91 of the button 90, the only resistance the user has to overcome is the angular displacement of the radial legs 73: such an angular displacement requires only very low force to be completed as it benefits from the natural gravitational force. The user needs not apply a high force on the button 90 in order to complete this step. The activation of the triggering means and the initiation of the insertion step of the needle is therefore very easy and simple: the user has no anxiety to face as the step proceeds very softly and smoothly.

The moving of the lever member 70 from its passive condition to its active condition frees the concentric double helical spring 8 which expands, as it automatically tries to reach a less stressed state than its first state, as shown on FIG. 10B. The button 90 therefore acts as triggering means for releasing the retaining means, namely the lever member 70. While expanding, the concentric double helical spring 8 produces a distal force along the axis of the longitudinal tubular lodging 23, said axis being parallel to the longitudinal axis A. The plunger rod 20, thanks to its bridge 22 and its shaft 21, is shaped and dimensioned so as to transmit this distal force to the syringe 2.

Because of the gliding resistance of the stopper 6, which is reinforced by the fact that the radial outer peg 26 of the plunger rod 20 is engaged in the flexible hook 13 of the syringe holder 10, the stopper 6 does not move with respect to the syringe 2, but the plunger rod 20, the syringe holder 10 and the syringe 2 are all driven in the distal direction, thereby realizing the insertion of the needle 3 into the injection site 10 (see FIG. 10B). The radial outer peg 26 of the plunger rod 20 and the flexible hook 13 of the syringe holder 10 therefore form maintaining means for maintaining the syringe 2 fixed with respect to the plunger rod 20 when the concentric double helical spring 8 goes from its first state to its second state. During this step, the concentric double helical spring 8 therefore acts as biasing means for moving the syringe 2 from its first position to its second position, said second position being an insertion position (needle inserted into the injection site).

In this position of the device 1 where the needle 3 is inserted in the injection site 10, and the distal end of the syringe 2 comes in abutment with the skin of the patient, the peg 12a of the syringe holder 10 has become engaged in a window of the proximal longitudinal groove 47 of the housing 40. As a consequence, the syringe holder 10 is now no more slidable with respect to the housing 40. The peg 12a and the window therefore act as fixing means for maintaining the syringe 2 in its second position with respect to the housing 40. Moreover, the distal movement of the syringe holder 10 with respect to the needle protection sleeve 30 has caused the helical spring 9 to reach an even more compressed state as shown on FIG. 10B.

As a consequence, from this step on, the syringe holder 10 will remain fixed with respect to the housing 40, and the removal of the device 1 from the skin of the patient will automatically cause the expansion of the helical spring 9 and therefore the movement of the needle protection sleeve 30 to its final position, in which it surrounds the needle (see FIG. 11). The device 1 of the invention is therefore very safe and requires no additional effort from the user for triggering the protection of the needle 3 as soon as the insertion step is completed, regardless from the fact that the injection step has started or not.

Once the needle is inserted, the concentric double helical spring 8 continues to expand towards a third state, less stressed than its second state, as shown on FIG. 10B. The force of the concentric double helical spring 8 causes the radial outer peg 26 of the plunger rod 20 to escape the flexible hook 13 of the syringe holder 10, thereby causing the distal movement of the stopper 6 within the syringe 2. The injection therefore takes place and the product 7 is expelled into the injection site 10 through the needle 3 until the stopper 6 reaches the distal end of the syringe 2 (see FIG. 10B).

During this step, the concentric double helical spring 8 acts as urging means for distally moving the stopper 6 once the syringe 2 has reached its second position, and therefore realize injection of the product 7. As such, in the example shown on these figures, the biasing means and the urging means are under the form of a concentric double helical spring, going from a first state to a second state, and then from said second state to a third state, said third state being less stressed than said second state, said second state being less stressed than said first state.

Whatever the necessary intrinsic force of the concentric double helical spring 8 for completing both the insertion step and the injection step, the effort required from the user at the beginning of the process for initiating the insertion step remains low thanks to the particular arrangement of the lever member 70.

In embodiments not shown, the biasing means and the urging means could be under the form of two different helical springs not concentric.

The user then removes the device 1 from the injection site, and, as already explained above, the helical spring 9 naturally expands from its compressed state to a rest state and causes the needle protection sleeve 30 to move distally with respect to the syringe 2 and to cover the needle 3, as shown on FIG. 11. The needle protection sleeve 30 therefore acts as needle protection means movable with respect to said housing 40 when the syringe 2 is fixed in its second position with respect to said housing 40 between an insertion position, in which the distal tip of the needle extends beyond the distal end of the needle protection means, and a final position, in which the distal tip of the needle does not extend beyond the distal end of the needle protection means and is surrounded by the needle protection means. During this step, the helical spring 9 acts as elastic return means for automatically moving said needle protection means (needle protection sleeve 30) from its insertion position to its final position, upon removal of the device 1 from the injection site 10 by the user.

FIGS. 12A-24 relate to an alternative embodiment of a device 101 of the invention. The references designating the same elements as for the device 1 of FIGS. 1A-11 have been maintained.

For sake of clarity, on FIG. 12A are shown only the plunger rod 120, the needle protection sleeve 130 with deactivating elements 135 and 136 attached thereto, the lever member 170 and the button 190 of device 101.

With reference to FIGS. 12A-24, the parts of the device 101 that differ from that of device 1 of FIGS. 1A-11 will now be described in details.

With reference to FIG. 13, is shown the plunger rod 120. The bridge 122 linking the lodging 123 to the shaft is provided on its side walls with a relief 124 which is a radial rounded peg 125. The plunger rod 122 further comprises a shaft 121 visible on FIGS. 23C and 24. The longitudinal axis of the shaft 121 and the longitudinal axis of the longitudinal tubular lodging 123 are parallel. A helical spring 108 (visible on FIGS. 23A-C and 24) is intended to be received within tubular lodging 123.

With reference to FIG. 14 is shown the needle protection sleeve 130 comprising a sleeve 131 having a proximal end 131a and a distal end 131b and a globally tubular shape. The sleeve 131 is provided on its outer wall with two opposite radial pegs 132 (only one being visible on FIG. 14). With reference to FIGS. 12A and 15, a longitudinal leg 135 is linked to the needle protection sleeve 130, by means of its distal end 135b facing radial peg 132. With reference to FIGS. 12A and 16A-16B, a longitudinal rod 136 is linked to the longitudinal leg 135 by means of its distal end 136b bearing on a proximal end 135a of the longitudinal leg 135. At its proximal end 136a, the longitudinal rod 136 is provided with a proximal side projection 137 having a sloped face 137a.

With reference to FIG. 17, the housing 140 comprises a tube 141 open at its proximal end 141a and its distal end 141b, capable of receiving the needle protection sleeve 130, as shown on FIGS. 23A-C. The tube 141 is provided on its wall with a cam 142 having a longitudinal track 142a and an oblique track 142b forming a bend 142c at their proximal ends. As shown on FIG. 20a, the radial peg 132 of the needle protection sleeve 130 is intended to be received within the cam 142 and to move therein.

With reference to FIG. 18, the lever member 170 comprises a pivoting part 171 rotatable around an axis R1. The pivoting part 171 is provided with two parallel tongues 172 extending in the radial direction with respect to axis R1. Each radial leg 172 is provided at its free end with a side peg 173. As will appear from the description below, as the pivoting part 171 rotates around its axis R1, the legs 172 describe a circle and are capable of changing angular positions. Each leg 172 forms an inner cavity 174 provided with a rounded recess 174a.

With reference to FIGS. 19A-B, the button 190 has the global shape of a cap 191 forming a pushing surface for the user: within the cap 191, the button 190 is provided with a pivoting part 192 rotatable around an axis R2. The cap 191 is further provided with two parallel longitudinal lateral walls 193 extending in a radial direction with respect to axis R2.

Each lateral wall 193 is provided with an inner curved groove 194, with a transversal abutment surface 195 and a distal abutment surface 196.

The operation of the device 101 of the invention will now be explained with reference to FIGS. 12A-24.

With reference to FIGS. 12A-12C, the device 101 is in a before use position. A helical spring 108 is lodged within the tubular lodging 123, with its distal end bearing on the proximal face of an inner distal rim 123c of the longitudinal tubular lodging 123, and the proximal end of the helical spring 108 bearing on a distal face of a top wall coupled to the housing 140 (see FIG. 23C). In the before use position as shown on FIGS. 12A-12C, the helical spring 108 is in a first state, which is a stressed state. As such, the helical spring 108 naturally tends to separate the plunger rod 120 from the housing 140. Nevertheless, the lever member 170 acts as retaining means for maintaining the helical spring 108 in its first stressed state as explained below.

Indeed, in the before use position, the radial rounded peg 125 of the plunger rod 120 is lodged in the rounded recess 174a of the inner cavity 174 of the lever member 170. The lever member 170 is fixed to the housing 140 (not visible on FIGS. 12A-B) via its pivoting part 171 and its side peg 173 is lodged at a proximal end of the curved groove 194 of the button 190 (see FIG. 12B). The side peg 173 is in distal abutment on the distal abutment surface 196 of the button 190 (see FIG. 12B), so that the lever member 170 is not allowed to rotate around its axis R1. In addition, as shown on FIG. 12A, the lever member 170 is positioned so as to have its rotatable pivoting part 171 included in a plane that is transversal with respect to the longitudinal axis of the longitudinal tubular lodging 123 of the plunger rod 120. The radial legs 172 have an angular position such that said radial legs 172 extend in a transversal direction from the pivoting part 171 (see FIGS. 12A and 12C).

The button 190 is pivotingly mounted on the housing 140 via its pivoting part 192. Anyway, in this before use position of the device 101, the sloped face 137a of the proximal side projection 137 of longitudinal rod 136 is in abutment against the transversal abutment 195 of the button, as shown on FIG. 12C. As a consequence, the button 190 is blocked in rotation, and pushing transversally on the cap 191 of the button 190 with a view to make it pivot will be unsuccessful.

As explained above, the lever member 170 acts as retaining means for maintaining the helical spring 108 in its first stressed state, and the lever member 170 is in a passive condition, as activation of the button 190 has no effect on the lever member 170 and therefore does not trigger the needle insertion step nor the injection of the product 7. The sloped surface 137a in abutment against transversal abutment 195 of the button 190 acts as locking means for preventing the triggering means (button 190) from moving the lever member 170 from its passive condition to its active condition.

As a consequence, for allowing the lever member 170 to be able to go from its passive condition to an active condition, in which the insertion of the needle 3 (see FIG. 23C) may be triggered, the user needs to apply the device 101 on his skin or on the skin of the patient via the distal end 131b of the distal sleeve 131 of the needle protection sleeve 130 (see FIG. 20A), and then push distally on the housing 140. As explained before, this movement causes the needle protection sleeve 130 to move proximally with respect to the housing 140. While the needle protection sleeve 130 moves proximally with respect to the housing 140, the radial peg 132, which was initially lodged at the distal end of oblique track 142b, moves in the proximal direction within said oblique track 142b and pushes proximally the distal end 135b of longitudinal leg 135, as shown on FIG. 20A. Furthermore, the longitudinal leg 135 is moved proximally and its proximal end 135a pushes proximally the longitudinal rod 136, as shown on FIG. 20A. As a consequence, the proximal side projection 137 of longitudinal rod 136 is moved distally, and its sloped surface 137a escapes from transversal abutment surface 195 of the button 190, as shown on FIG. 20B.

The button 190 is therefore no more blocked in rotation. The user pushes transversally on the cap 191 of the button 190 in the direction of the arrow F shown on FIG. 21A and the button 190 pivots around its axis R2. Only low force is required from the user for pushing cap 191, as the button 190 is pivotingly mounted onto the housing 140. The pivoting of cap 191 causes the side peg 173 to escape distal abutment surface 196 of the button 190 and to enter into the proximal end of curved groove 194, as shown on FIG. 21B.

The gravitational force therefore causes side peg 173 to automatically move distally within curved groove 194, as shown on FIG. 22B, and the radial legs 172 move from their first angular position, as shown on FIG. 22A, to a second angular position, as shown on FIGS. 23A and 23B, in which they extend in the distal direction. As a consequence of the radial legs 172 reaching their second angular position, the radial rounded peg 125 of the plunger rod 120 escapes the rounded recess 174a of the inner cavity 174 of the lever member 170 and the helical spring 108 is released, as shown on FIGS. 23A-C.

As appears from the above, the angular displacement of the radial legs 172 is caused automatically and naturally by the gravitational force. As a consequence, the user needs not apply a high force on the button 190 in order to trigger injection. The activation of the triggering means and the initiation of the insertion step of the needle is therefore very easy and simple: the user has no difficulties to face as the step proceeds very softly and smoothly.

While expanding, the helical spring 108 produces a distal force along the axis of the longitudinal tubular lodging 123, said axis being parallel to the longitudinal axis A. The plunger rod 120, thanks to its bridge 122 and its shaft 121 (see FIGS. 23C and 24), is shaped and dimensioned so as to transmit this distal force to the syringe 2. Insertion of the needle 3 is therefore completed.

The injection step is automatically completed in the same manner as that described for device 1 of FIGS. 1A-11. Also in the same way as described for device 1 of FIGS. 1A-11, removal of the device 101 from the injection site causes helical spring 109 to naturally expand from its compressed state to a rest state, thereby causing the needle protection sleeve 130 to move distally with respect to the syringe 2 and to cover the needle 3, as shown on FIG. 24.

Like device 1 of FIGS. 1A-11, the device 101 of FIGS. 12A-24 may have its motor part and its housing part 140 manufactured separately, and then assembled.

The device of the invention allows having biasing means, such as the concentric double helical spring 8 of embodiment of FIGS. 1A-11 or helical spring 108 of embodiment of FIGS. 12A-24 having a high intrinsic force for completing the injection of products requiring such a high distal force, such as viscous drugs, while at the same time requiring only a low force from the user at the time of triggering the injection.

The invention claimed is:

1. A device for injection of a product into an injection site, said device comprising:
  a housing having a longitudinal axis A,
  a container located within the housing, said container capable of holding the product to be injected, said container including a proximal end and a distal end,
  a stopper located at the proximal end of the container for substantially closing the proximal end of the container, said stopper capable of being moved in a distal direction within the container to expel the product to be injected,
  a needle located at the distal end of the container, said needle configured to allow the product to exit there through, said container being movable with respect to said housing between a first position, in which the needle does not extend beyond a distal end of the housing, and a second position, which is distally spaced with respect to said first position, in which the needle extends beyond the distal end of the housing, a biasing member, coupled to said container and to said housing during movement of the container at least from said first position to said second position, said biasing member designed for exerting a distal force to said container so as to move said container from the first position to the second position when the biasing member transitions from a first state to a second state, wherein said second state is less stressed than said first state, a retaining device coupled to said container and to said housing when the container is in the first position, for releasably maintaining said biasing member in the first state, said retaining device being capable of moving from a passive condition, in which the retaining device maintains said biasing member in its first state, to an active condition, in which said biasing member is free to expand to its second state, a trigger capable of moving said retaining device from its passive condition to its active condition, wherein said retaining device comprises a lever member having a pivoting part rotatable around an axis RI and at least a radial projection extending from said pivoting part, said radial projection being in a first angular position when said retaining device is in its passive condition, said radial projection being in a second angular position, different from said first angular position, when said retaining device is in its active condition, said axis R1 of said pivoting part being included in a transversal plane of said longitudinal axis A.

2. The device of claim 1, wherein said biasing member is a spring linked to said stopper via a plunger rod, said device further comprising a releasable maintaining member for maintaining said container fixed with respect to said plunger rod when said spring transitions from its first state to its second state, said maintaining member being released when said spring reaches its second state.

3. The device of claim 2, wherein the spring is a concentric double helical spring.

4. The device of claim 2, wherein said maintaining member comprises a hook fixed with respect to said container, said hook trapping a peg located on said plunger rod, wherein the peg is only allowed to escape from said hook under the force of the spring when said container has reached its second position and said spring is in its second state.

5. The device of claim 1, wherein, in its first angular position, the radial projection extends in an oblique or transversal direction with respect to the distal direction, and in its second angular position, the radial projection extends in the distal direction.

6. The device of claim 1, wherein said trigger comprises a button mounted in pivoting relationship with respect to said housing, said button comprising a pushing surface accessible to a user for pivoting said button, said button further comprising an actuating surface capable of cooperating with said lever member for moving said radial projection from its first angular position to its second angular position, when the button is caused to pivot.

7. The device of claim 6, wherein the actuating surface comprises an edge of said button cooperating with said pivoting part of said lever member when the button is caused to pivot.

8. The device of claim 6, wherein the actuating surface comprises a groove of said button cooperating with a peg of said radial projection of said lever member, when the button is caused to pivot.

9. The device of claim 1, further comprising:
a locking member for preventing said trigger from moving said retaining device from its passive condition to its active condition, said locking member being releasable, and
a deactivating member for releasing the locking member.

10. The device of claim 9, wherein the locking member comprises a movable surface of said device, said surface being movable between a first position, in which said surface prevents cooperation between said lever member and said button, to a second position, in which said surface allows cooperation between said lever member and said button, said movable surface being caused to move from its first position to its second position by said deactivating member.

11. The device of claim, wherein said deactivating member is capable of transitioning from a before use position, in which it does not release the locking member, to an active position in which it releases the locking member and the trigger may be activated, the device further comprising a storage elastic return member for urging said deactivating member back in its before use position as long as the trigger has not been activated.

12. The device of claim 1, further comprising:
a fixing member for maintaining said container in its second position with respect to said housing, and
an urging member coupled to said stopper and to said housing when said container is in its second position, said urging member configured for distally moving said stopper when transitioning from a first state to a second state, said second state being less stressed than said first state, thereby resulting in injection of the product.

13. The device (1; 101) of claim 12, wherein said spring is further capable of transitioning from its second state to a third state, during which said spring moves the stopper distally, said third state being less stressed than said second state, and wherein said spring forms both said biasing member and said urging member.

14. The device of claim 12, wherein the fixing member comprises a peg fixed with respect to said container and a window located on said housing, said peg being locked within said window when said container is in its second position with respect to said housing.

15. The device of claim 1, further comprising:
a needle protection member, at least partially received within said housing, and movable with respect to said housing when said container is fixed in its second position with respect to said housing between an insertion position, in which a distal tip of the needle extends beyond the distal end of the needle protection member, and a final position, in which the distal tip of the needle does not extend beyond the distal end of the needle protection member, and
an elastic return member, coupled to said needle protection member and to said container, and designed for automatically moving said needle protection member from its insertion position to its final position, upon removal of the device from an injection site by a user.

16. The device of claim 9, wherein in the first position of the container with respect to the housing, said needle protection member is movable with respect to said housing between a before use position and a use position, said use position being proximally spaced with respect to said before use position, and wherein at least part of said needle protection member forms said deactivating member.

17. The device of claim 1, wherein said biasing member is positioned so as to produce a distal force along an axis parallel to said longitudinal axis A, said device further comprising a linking member coupled to said biasing member and to said container, said linking member being shaped and dimensioned so as to transmit said distal force to said container.

18. The device of claims 2, wherein said plunger rod forms said linking member, said plunger rod comprising a shaft aligned on said longitudinal axis A, said shaft being provided at its distal end with said stopper, a bridge linking a proximal end of said shaft to a proximal end of a lateral tubular lodging parallel to said longitudinal axis A and receiving said spring, said spring being in distal abutment on a distal transversal wall of said tubular lodging and being in proximal abutment on a proximal transversal wall fixed with respect to said housing.

19. The device of claim 9, wherein said device is under the form of two autonomous connectable parts, said connectable parts comprising a motor part and a housing part,
- said motor part comprising at least said biasing member, said retaining device, said triggering trigger, and said urging member,
- said housing part comprising at least said housing, said deactivating member, said fixing member, said needle protection member, and said elastic return member,
- said locking member being located on one of said motor part and housing part, said device further comprising a connecting member for connecting said motor part to said housing part at the time of use.

\* \* \* \* \*

UNITED STATES PATENT AND TRADEMARK OFFICE
CERTIFICATE OF CORRECTION

PATENT NO. : 9,533,099 B2  Page 1 of 1
APPLICATION NO. : 14/426336
DATED : January 3, 2017
INVENTOR(S) : Lionel Maritan It is certified that error appears in the above-identified patent and that said Letters Patent is hereby corrected as shown below:

In the Claims

Column 19, Line 22, Claim 1, delete "RI" and insert -- R1 --

Column 20, Line 15, Claim 11, delete "claim," and insert -- claim 9, --

Column 20, Line 32, Claim 13, after "device" delete "(1; 101)"

Column 21, Line 19, Claim 19, after "said" delete "triggering"

Signed and Sealed this
Twenty-eighth Day of February, 2017

Michelle K. Lee
*Director of the United States Patent and Trademark Office*